US010956701B2

(12) United States Patent
Laviola et al.

(10) Patent No.: US 10,956,701 B2
(45) Date of Patent: Mar. 23, 2021

(54) SYNCHRONIZED SURFACE AND INTERNAL TUMOR DETECTION

(71) Applicant: HOLOGIC, INC., Marlborough, MA (US)

(72) Inventors: John Laviola, Marlborough, MA (US); Julian Marshall, Marlborough, MA (US); Bob Brody, Marlborough, MA (US); Kenneth F. Defreitas, Marlborough, MA (US)

(73) Assignee: HOLOGIC, INC., Marlborough, MA (US)

( * ) Notice: Subject to any disclaimer, the term of this patent is extended or adjusted under 35 U.S.C. 154(b) by 124 days.

(21) Appl. No.: 16/304,542

(22) PCT Filed: May 23, 2017

(86) PCT No.: PCT/US2017/034022
§ 371 (c)(1),
(2) Date: Nov. 26, 2018

(87) PCT Pub. No.: WO2017/205386
PCT Pub. Date: Nov. 30, 2017

(65) Prior Publication Data
US 2019/0251327 A1 Aug. 15, 2019

Related U.S. Application Data

(60) Provisional application No. 62/342,713, filed on May 27, 2016.

(51) Int. Cl.
*G06K 9/00* (2006.01)
*G06T 7/00* (2017.01)
(Continued)

(52) U.S. Cl.
CPC .......... *G06K 9/00013* (2013.01); *A61B 6/502* (2013.01); *A61B 6/5247* (2013.01);
(Continued)

(58) Field of Classification Search
CPC .............. G06K 9/00013; G06T 7/0012; G06T 2207/20104; G06T 2207/10112;
(Continued)

(56) References Cited

U.S. PATENT DOCUMENTS 3,908,293 A 9/1975 Newman
3,971,950 A 7/1976 Evans
(Continued)

FOREIGN PATENT DOCUMENTS

DE 103 05 640 8/2003
JP 2003-527880 9/2003
(Continued)

OTHER PUBLICATIONS

European Extended Search Report in Application 17803431.0, dated Dec. 11, 2019, 14 pages.
(Continued)

*Primary Examiner* — Jon Chang

(57) ABSTRACT

A method for imaging includes acquiring surface image data for a target using a first imaging modality. A visual representation of the target based on the surface image data is generated. Internal image data for the target is acquired using a second imaging modality. During acquisition of the internal image data, the visual representation of the target based on the acquired internal image data is updated.

20 Claims, 14 Drawing Sheets

(51) Int. Cl.
*A61B 8/08* (2006.01)
*A61B 6/00* (2006.01)
*A61B 5/00* (2006.01)
*A61B 8/00* (2006.01)

(52) U.S. Cl.
CPC .......... *A61B 8/0825* (2013.01); *A61B 8/5261* (2013.01); *G06T 7/0012* (2013.01); *A61B 5/0064* (2013.01); *A61B 5/0077* (2013.01); *A61B 8/461* (2013.01); *G06T 2200/04* (2013.01); *G06T 2207/10012* (2013.01); *G06T 2207/10081* (2013.01); *G06T 2207/10112* (2013.01); *G06T 2207/10116* (2013.01); *G06T 2207/10132* (2013.01); *G06T 2207/20104* (2013.01); *G06T 2207/30068* (2013.01)

(58) Field of Classification Search
CPC ....... G06T 2200/04; G06T 2207/10116; G06T 2207/10081; G06T 2207/10012; G06T 2207/10132; G06T 2207/30068; A61B 6/502; A61B 6/5247; A61B 8/0825; A61B 5/7275; A61B 5/7264; A61B 8/5261; A61B 8/461; A61B 8/54; A61B 8/4263; A61B 8/466; A61B 5/0064; A61B 5/0077
See application file for complete search history.

(56) References Cited

U.S. PATENT DOCUMENTS

| | | | |
|---|---|---|---|
| 4,907,156 A | 6/1990 | Doi | |
| 5,133,020 A | 7/1992 | Giger | |
| 5,220,867 A | 6/1993 | Carpenter | |
| 5,289,374 A | 2/1994 | Doi | |
| 5,343,390 A | 8/1994 | Doi | |
| 5,452,367 A | 9/1995 | Bick | |
| 5,474,072 A | 12/1995 | Schmulewitz | |
| 5,479,603 A | 12/1995 | Stone | |
| 5,491,627 A | 2/1996 | Zhang | |
| 5,495,576 A | 2/1996 | Ritchey | |
| 5,537,485 A | 7/1996 | Nishikawa | |
| 5,657,362 A | 8/1997 | Giger | |
| 5,729,471 A | 3/1998 | Jain | |
| 5,851,180 A | 12/1998 | Crosby | |
| 5,999,662 A | 12/1999 | Burt | |
| 6,044,181 A | 3/2000 | Szeliski et al. | |
| 6,075,905 A | 6/2000 | Herman et al. | |
| 6,104,840 A | 8/2000 | Ejiri et al. | |
| 6,198,838 B1 | 3/2001 | Roehrig | |
| 6,249,616 B1 | 6/2001 | Hashimoto | |
| 6,263,092 B1 | 7/2001 | Roehrig | |
| 6,349,153 B1 | 2/2002 | Teo | |
| 6,359,617 B1 | 3/2002 | Xiong | |
| 6,725,095 B2 | 4/2004 | Fenn | |
| 7,054,473 B1 | 5/2006 | Roehrig | |
| 7,123,684 B2 | 10/2006 | Jing et al. | |
| 7,134,080 B2 | 11/2006 | Kjeldsen | |
| 7,174,039 B2 | 2/2007 | Koo | |
| 7,245,694 B2 | 7/2007 | Jing et al. | |
| 7,489,761 B2 | 2/2009 | Clause | |
| 7,505,555 B2 | 3/2009 | Hermann | |
| 7,702,142 B2 | 4/2010 | Ren | |
| 7,731,662 B2 | 6/2010 | Anderson et al. | |
| 8,160,677 B2 | 4/2012 | Gielen et al. | |
| 8,192,361 B2 | 6/2012 | Sendai | |
| 8,465,413 B2 | 6/2013 | Deitch | |
| 8,942,342 B2 | 1/2015 | Abenaim | |
| 9,019,262 B2 | 4/2015 | Ma et al. | |
| 9,160,793 B2 | 10/2015 | Base et al. | |
| 9,901,320 B2 | 2/2018 | DeFreitas et al. | |
| 2001/0044578 A1 | 11/2001 | Ben-Haim et al. | |
| 2003/0007598 A1 | 1/2003 | Wang et al. | |
| 2003/0055471 A1 | 3/2003 | Fenn et al. | |
| 2003/0194050 A1 | 10/2003 | Eberhard et al. | |
| 2004/0077944 A1 | 4/2004 | Steinberg | |
| 2005/0089205 A1 | 4/2005 | Kapur | |
| 2005/0108643 A1 | 5/2005 | Schybergson | |
| 2006/0074287 A1 | 4/2006 | Neumann | |
| 2006/0126794 A1 | 6/2006 | Hermann et al. | |
| 2006/0178601 A1 | 8/2006 | Wang et al. | |
| 2007/0167709 A1 | 7/2007 | Slayton | |
| 2007/0232882 A1 | 10/2007 | Glossop | |
| 2007/0280412 A1 | 12/2007 | DeFreitas | |
| 2008/0181361 A1 | 7/2008 | Eldered | |
| 2008/0242968 A1 | 10/2008 | Claus et al. | |
| 2009/0024030 A1* | 1/2009 | Lachaine ............ A61B 8/4416 600/437 |
| 2009/0118614 A1 | 5/2009 | Sendai | |
| 2009/0124906 A1 | 5/2009 | Caluser | |
| 2009/0175408 A1 | 7/2009 | Goodsitt et al. | |
| 2010/0016707 A1 | 1/2010 | Amara et al. | |
| 2010/0166147 A1 | 7/2010 | Abenaim | |
| 2010/0284591 A1 | 11/2010 | Arnon et al. | |
| 2011/0313288 A1 | 12/2011 | Chi Sing | |
| 2012/0035462 A1 | 2/2012 | Maurer et al. | |
| 2012/0150034 A1 | 6/2012 | DeFreitas et al. | |
| 2012/0256920 A1 | 10/2012 | Marshall et al. | |
| 2012/0302887 A1 | 11/2012 | Anderson et al. | |
| 2015/0051489 A1 | 2/2015 | Caluser et al. | |
| 2015/0182191 A1 | 7/2015 | Caluser et al. | |
| 2018/0125446 A1* | 5/2018 | Boroczky ............ G06T 7/0012 |
| 2018/0249985 A1 | 9/2018 | DeFreitas | |

FOREIGN PATENT DOCUMENTS

| | | |
|---|---|---|
| JP | 2005125080 | 5/2005 |
| JP | 2007-515242 | 6/2007 |
| JP | 2008518722 | 6/2008 |
| JP | 2009502347 | 1/2009 |
| JP | 2009-518722 | 5/2009 |
| WO | 2012/073164 A1 | 6/2012 |

OTHER PUBLICATIONS

Vaartjes, S.E., et al., "First clinical trials of the Twente photoacoustic mammoscope (PAM)", Visual Communications and Image Processing; Jan. 20, 2004-Jan. 20, 2004; San Jose, CA, USA, vol. 6629, Jan. 1, 2007, pp. 1-12.

Blane, C. et al., "New Compression Paddle for Wire Localization in Mammography", Academic Radiology, 17(2): 142-145 (2010).

Bram Van Ginneken, Computer-aided Diagnosis in Chest Radiography Thesis, Image Sciences Institute, University Medical Center Utrecht, Utrecht, Netherlands, (2010).

Carson, P. et al., "Local compression in automated breast ultrasound in the mammographic geometry", Ultrasonics Symposium, 1787-1790 (2010).

European Extended Search Report for corresponding European Patent Application No. 11848276.9 dated Aug. 9, 2016, 13 pgs.

Giger et al., An Intelligent Workstation for Computer Aided Diagnosis, RadioGraphics May 1993, vol. 13, pp. 647-656.

Giger et al., Development of a Smart Workstation for Use in Mammography, SPIE, vol. 1445, 1991, pp. 101-103.

Gutierrez et al., "Multimodality image guidance system integrating X-ray fluoroscopy and ultrasound image streams with electromagnetic tracking", Medical Imaging 2007: Visualization and Image-Guided Procedures, Proc. of SPIE vol. 6509, 2007, pp. 1-10.

PCT International Search Report and Written Opinion for PCT/US2011/064847, dated Jun. 7, 2012.

PCT International Preliminary Report on Patentability for PCT/US2011/064847, dated Jun. 18, 2013, 8 pages.

International Search Report and Written Opinion of the International Searching Authority for International Patent Application No. PCT/US2017/034022 dated Aug. 22, 2017, 9 pages.

* cited by examiner

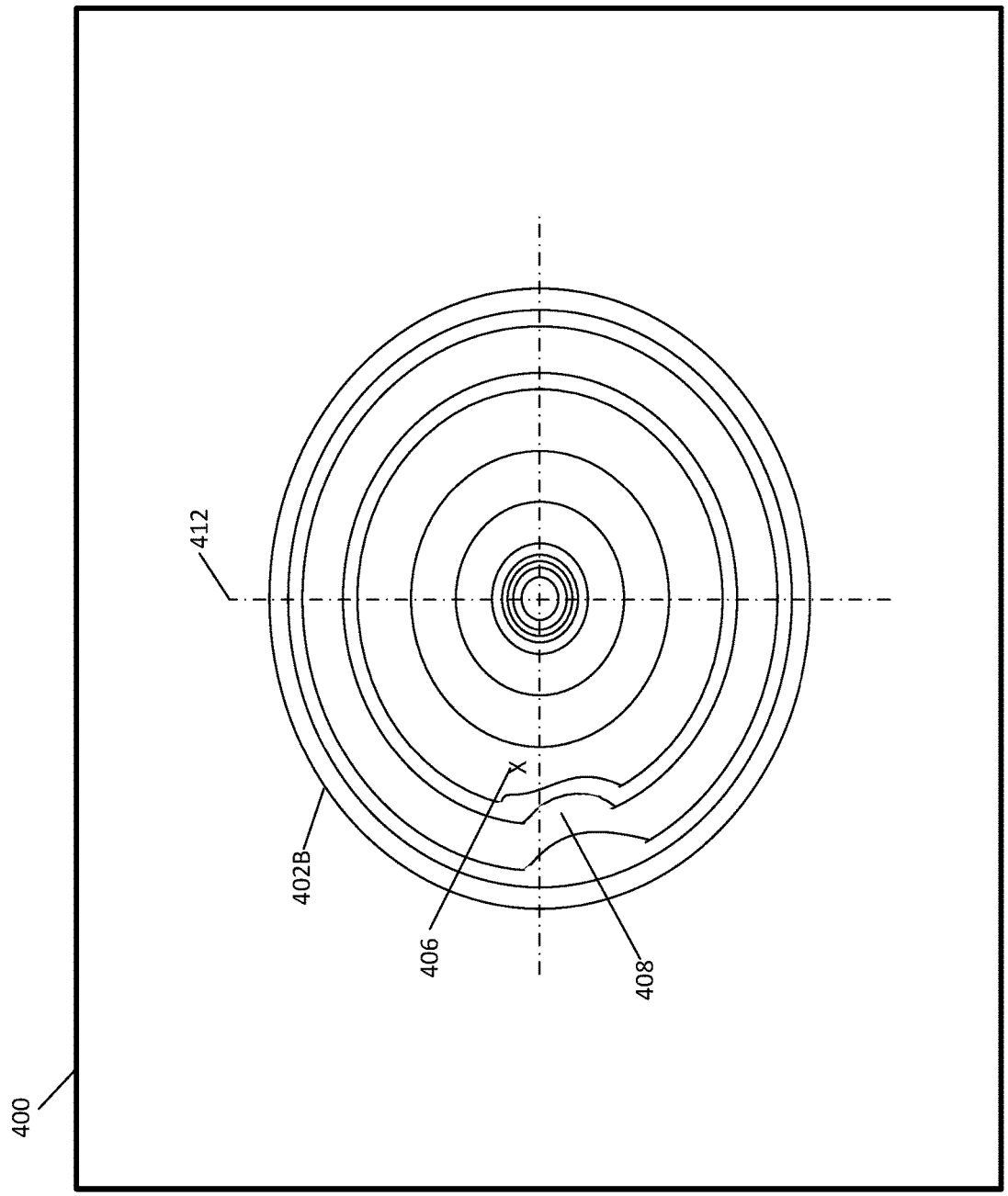

SYNCHRONIZED SURFACE AND INTERNAL TUMOR DETECTION

CROSS-REFERENCE TO RELATED APPLICATIONS

This application is a National Stage Application of PCT/US2017/034022, filed May 23, 2017, which claims priority to U.S. Provisional Patent Application No. 62/342,713, filed May 27, 2016, which are incorporated herein by reference in their entireties. To the extent appropriate, a claim of priority is made to each of the above disclosed applications.

BACKGROUND

Medical imaging devices provide non-invasive methods to visualize the internal structure of a patient. Such non-invasive visualization methods can be helpful in treating patients for various ailments. For example, the early detection of cancer or tumors in a patient can be important in treating that patient, and may increase survival probability of patients.

Ultrasound imaging, a non-invasive medical imaging technique, uses sound waves, typically produced by piezoelectric transducers, to image a tissue in a patient. The ultrasound probe focuses the sound waves, typically producing an arc-shaped sound wave which travels into the body and is partially reflected from the layers between different tissues in the patient. The reflected sound wave is detected by the transducers and converted into electrical signals that can be processed by the ultrasound scanner to form an ultrasound image of the tissue.

The typical procedure followed to obtain ultrasound images of a patient's breast involves positioning a patient in a supine position upon a table, applying a gel or other acoustic couplant to the patient's breast, and passing an ultrasound transducer across the patient's breast. As the transducer traverses the breast, ultrasound images can typically be viewed in real-time on a display of an ultrasound system. The ultrasound transducer may be either a hand-held transducer which is manually manipulated by the imaging technician, or may be an automated scanning device, such as that described in U.S. Pat. No. 7,731,662. While ultrasound scanning has desirable sensitivity in detecting internal structures, a handheld ultrasound probe suffers generally poor location specificity. For instance, one drawback of such methods lies in the fact that the breast is a very malleable structure; the geometry and structures of the breast move and change whenever the patient changes position. Thus, accurate and thorough scanning of the breast with an ultrasound probe is difficult to achieve.

SUMMARY

In one aspect, the technology relates to a method for imaging, the method including: acquiring surface image data for a target using a first imaging modality; generating a visual representation of the target based on the surface image data; acquiring internal image data for the target using a second imaging modality; and during the acquiring of the internal image data, updating the visual representation of the target based on the acquired internal image data. In an embodiment, the target includes a breast. In another embodiment, the first imaging modality is at least one of digital photography, structured light stereoscopic photography, and infrared imaging. In yet another embodiment, the second imaging modality is ultrasound imaging. In still another embodiment, the method further includes identifying a region of interest on the surface of the target based on the visual representation.

In another embodiment of the above aspect, the method further includes displaying the region of interest in the visual representation. In an embodiment, the method further includes: acquiring updated surface image data of the target by the first imaging modality when the target is deformed by the second imaging modality during acquisition of the internal image data; generating an updated visual representation of the deformed target based on the updated surface image data; and displaying the updated visual representation during acquisition of the internal image data.

In another aspect, the technology relates to a method for imaging a breast of a patient, the method includes: acquiring a photographic image of a surface of the breast; based on the photographic image, generating a surface map of the breast; displaying a visual representation of the breast; identifying a region of interest on the surface of the breast based on the visual representation; displaying the visual representation of the breast with an indicator indicating the identified region of interest; acquiring ultrasound images of the breast with an ultrasound probe; and during acquisition of the ultrasound images, updating the display of the visual representation based at least in part on the acquired ultrasound images. In an embodiment, updating the display of the visual representation includes displaying in the visual representation portions of the breast scanned by the ultrasound probe. In another embodiment, the method further includes analyzing the acquired ultrasound images of the breast to identify an additional region of interest of the breast for scanning with the ultrasound probe, and wherein updating the display of the visual representation includes identifying in the visual representation the additional region of interest of the breast. In yet another embodiment, the method further includes generating feedback regarding at least one of an angle of the ultrasound probe, an orientation of the ultrasound probe, a position of the ultrasound probe, and a scan velocity of the ultrasound probe. In still another embodiment, the photographic image is a stereoscopic structured light image of the breast.

In another embodiment of the above aspect, the method further includes analyzing at least one of the acquired ultrasound image and the photographic image to determine an anomalous breast architecture. In an embodiment, the method further includes generating a three-dimensional model based on the ultrasound images, wherein the three-dimensional model includes an indicator indicating the location of the anomalous breast architecture. In another embodiment, the method further includes analyzing at least one of the acquired ultrasound image and the photographic image to generate a cancer risk score for the breast. In yet another embodiment, identifying the region of interest is based on at least one of an ipsilateral skin texture, a contralateral skin texture, a skin color, a tissue dimpling, a nipple change, an inverted nipple, a lump, and a contralateral breast volume difference. In still another embodiment, the method further includes: acquiring an updated photographic image of the breast when the breast is deformed by the ultrasound probe during acquisition of the ultrasound images; generating an updated visual representation of the deformed breast based on the second photographic image; and displaying the updated visual representation of the deformed breast during acquisition of the ultrasound images.

In another embodiment of the above aspect, the visual representation includes at least one of the photographic image and the surface map. In an embodiment, the breast is uncompressed during acquisition of the ultrasound images.

In another aspect, the technology relates to a system for imaging a breast of a patient, the system includes: a camera; an ultrasound probe; a display; at least one processor; and memory operatively coupled to the at least one processor, the memory storing instructions that, when executed by the at least one processor, perform a set of operations including: generating a surface map of the breast based on a photographic image acquired by the camera; identifying a region of interest on the surface of the breast based on a visual representation of the breast; generating a surface indicator on the visual representation, wherein the surface indicator indicates the identified region of interest; sending the visual representation with the surface indicator to the display; receiving ultrasound images of the breast from the ultrasound probe; during acquisition of the ultrasound images, generating an update to the display of the visual representation based on the acquired ultrasound images; and sending the update to the display. In an embodiment, the system further includes a tracking system operatively connected to the ultrasound probe and communicatively connected to the at least one processor. In another embodiment, the update includes a graphical representation on the visual representation representing a portion of the breast scanned by the ultrasound probe. In yet another embodiment, the update includes a graphical representation on the visual representation representing another region of interest of the breast to be scanned with the ultrasound probe. In still another embodiment, the camera is a stereoscopic camera and the photographic image is a stereoscopic structured light image of the breast.

In another embodiment of the above aspect, the set of operations further includes analyzing at least one of the acquired ultrasound images and the photographic image to determine an anomalous breast architecture. In an embodiment, identifying the region of interest is based on at least one of an ipsilateral a skin texture, a contralateral skin texture, a skin color, a tissue dimpling, a nipple change, an inverted nipple, a lump, and a contralateral breast volume difference. In another embodiment, the set of operations further includes, based on one or more of the surface map and the acquired ultrasound images, generating feedback regarding at least one of an angle of the ultrasound probe, an orientation of the ultrasound probe, a position of the ultrasound probe, and a scan velocity of the ultrasound probe. In yet another embodiment, the system further includes a speaker and wherein the set of operations further includes: analyzing the acquired ultrasound images; based on the analysis of the acquired ultrasound images, sending an audio signal to the speaker to provide an audible feedback. In still another embodiment, the set of operations further include: acquiring an updated photographic image of the breast when the breast is deformed by the ultrasound probe during acquisition of the ultrasound images; generating an updated visual representation of the deformed breast based on the second photographic image; and sending the updated visual representation of deformed breast to the display during acquisition of the ultrasound images.

In another aspect, the technology relates to a method for imaging a breast of a patient, the method includes: acquiring a photographic image of a breast using a camera; displaying a visual representation of the breast, wherein the visual representation is based at least on the photographic image; scanning the breast with an ultrasound probe; and while scanning, tracking the location of the ultrasound probe and updating the displayed visual representation based on the tracked location of the ultrasound probe.

In another aspect, the technology relates to a method for imaging a breast of a patient, the method includes: acquiring a first photographic image of a breast; displaying a visual representation of the breast, wherein the visual representation is based at least on the first photographic image; scanning the breast with an ultrasound probe, wherein scanning the breast causes the breast to deform; and while scanning the breast: acquiring a second photographic image of the breast, the second photographic image depicting the deformed breast; and displaying a second visual representation of the breast, wherein the second visual representation is based at least on the second photographic image.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

FIGS. 4A-4C depict examples of a displayed visual representation of a breast during acquisition of internal image data.

DETAILED DESCRIPTION

The present technology relates to methods and systems suitable for imaging a target with a first imaging modality and a second imaging modality. The first imaging modality may capture image data for a surface of the target and the second imaging modality may capture image data for internal aspects of a target. Feedback may also be provided to a technician during the image acquisition process. In an example, a photographic image is taken of a target, such as a breast. The photographic image is, optionally, then analyzed to determine potential high-risk areas or regions of interest on the surface of the breast. From the photographic image, a visual representation of the breast may also be generated and displayed on a display screen for the technician (e.g., a medical professional) to view. The visual representation may also include indicators indicating the identified high-risk areas or regions of interest. The medical professional may then use the visual representation as a guide for utilizing the second imaging modality, such as, but not limited to, ultrasound imaging. In general, the second imaging modality includes imaging of internal aspects of the breast from an external device. Such imaging with be referred to herein as internal imaging, as contrasted with intra-cavity imaging, where an imaging device is inserted into tissue for imaging thereof. As the medical professional uses the ultrasound probe, the display of the visual representation is updated to reflect the progress of the ultrasound imaging. For example, portions of the breast that have been scanned by the ultrasound probe may be highlighted. Alternatively, any indicia (e.g., markers, colors, icons, etc.) that can be used to represent that a portion of the breast has been imaged with the second imaging modality may be utilized. Additionally, updated photographs of the breast may be acquired during the ultrasound scanning, and those updated photographs may be used to update the visual representation to reflect any current deformations of the breast caused by the ultrasound probe. Such a system is able to provide substantially real-time information about the internal imaging process to provide more thorough and accurate internal imaging. Accordingly, accurate location tracking of ultrasound imaging may be achieved even with an uncompressed or unfixed breast.

Other multi-modality screening systems are described in U.S. Patent Publication No. 2012/0150034, titled "System and Method for Fusing Three Dimensional Image Data from a Plurality of Different Imaging Systems for Use in Diagnostic Imaging," is related to the present application, and the entirety of that application is incorporated herein by reference.

Figure 1A:
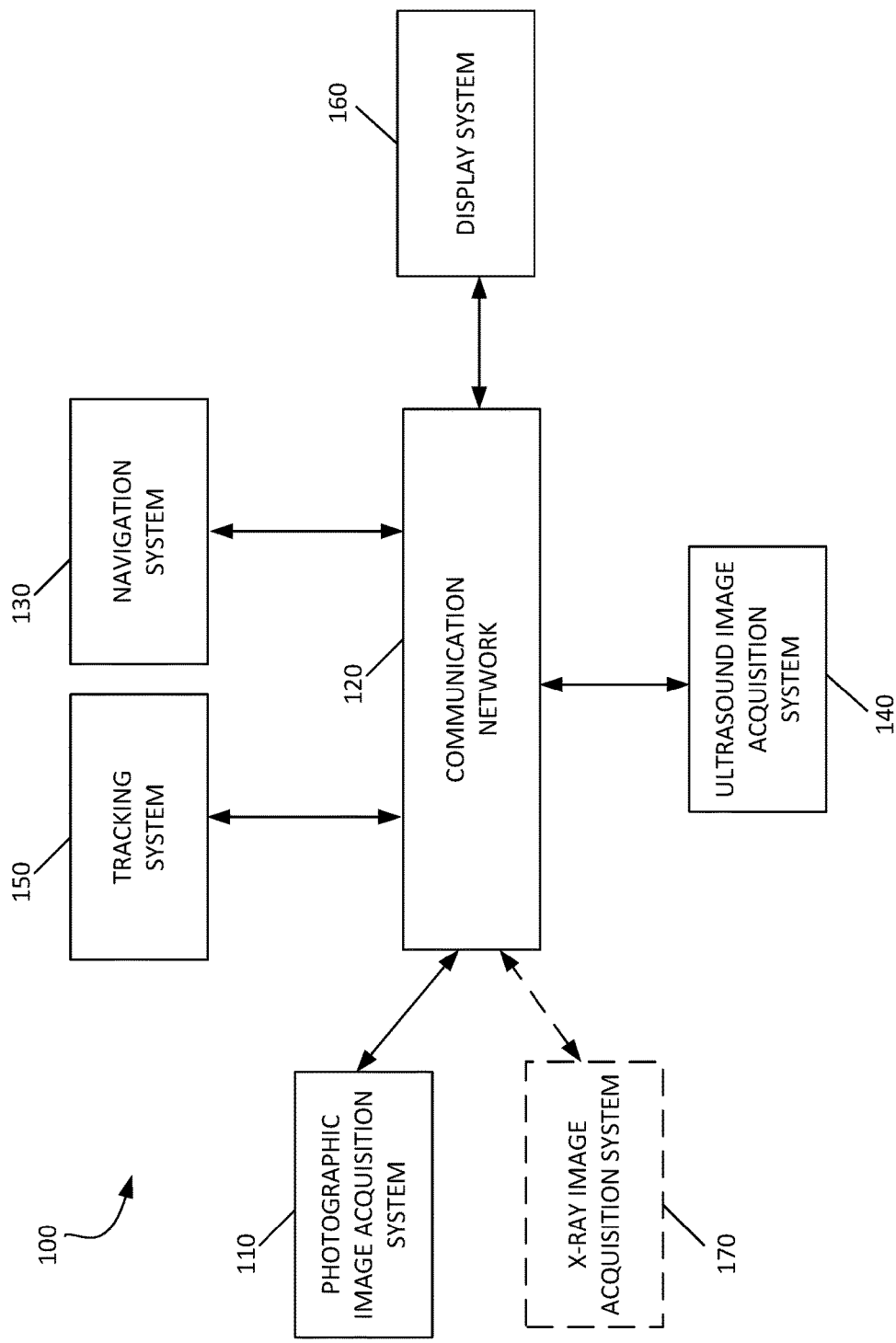
FIGS. 1A-1B depict systems for facilitating screening with a surface imaging modality and at least one internal imaging modality.
Figure 1B:
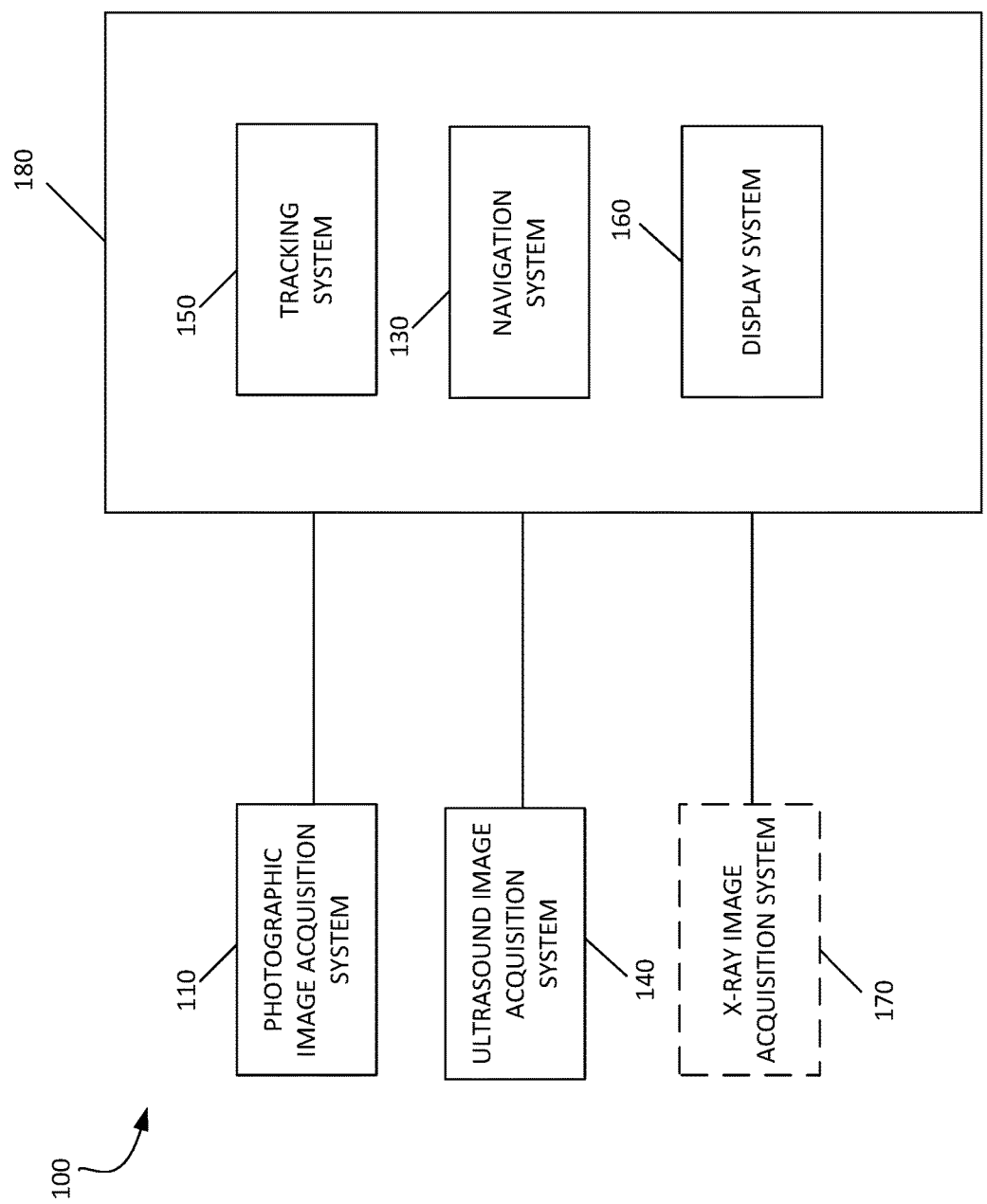

FIGS. 1A and 1B depict a system 100 for facilitating screening with a surface imaging modality and at least one internal imaging modality. System 100 includes photographic image acquisition system 110, an ultrasound image acquisition system 140, a tracking system 150, an optional navigation system 130, a display system 160, and, optionally, an x-ray image acquisition system 170, all representatively connected via a communication network 120. It should be noted that, although FIG. 1A depicts discrete systems as functional blocks in the overall system 100, certain of those discrete systems may be integrated into a common device 180 as depicted in FIG. 1B. For example, the tracking system 150, the navigation system 130, and the display system 160 may be included in the common device 180, while the remaining systems may be in communication with the common device 180, e.g., via wireless or wired communication. The common device 180 may be a computer, one or more discrete computers, an acquisition work station, a technologist work station, or any other devices where a technician can control, operate, etc., the common device 180 and/or connected systems. In an example, the device 180 may be a portable device with a display system 160, user interface, power module (to connect to building, solar, and/or battery power), and may include inputs for attaching the photographic image acquisition system 110, the ultrasound image acquisition system 140, and, optionally, the x-ray image acquisition system 170. In another example, the navigation system 130 and the tracking system 150 may be integrated into the ultrasound image acquisition system 140, or provided as standalone modules with separate communication links to the display 160, photographic image acquisition system 110, and ultrasound image acquisition system 140. Similarly, skilled persons will additionally appreciate that communication network 120 may be a local area network, wide area network, wireless network, wired network, internet, intranet, or other similar communication network.

Photographic image acquisition system 110 obtains at least one photographic image of the surface of the breast. In some embodiments, the photographic image is a basic digital photograph of the breast captured from a digital camera, or may be a frame or image captured from a digital video camera. In other embodiments, the photographic image is a stereoscopic image captured by a stereoscopic digital camera. In further embodiments, the photographic image is a stereoscopic image captured with a stereoscopic digital camera using structured light techniques. Structured light techniques operate by projecting a light pattern onto the breast and capturing a stereoscopic photograph of the breast having the projected light pattern. Upon analysis of the changes to the structured light pattern based on the curvature and shape of the breast, the three-dimensional parameters for the surface of the breast are determined. As used herein, a photographic image may be any image of the surface of the target. In some embodiments, the photographic image can additionally be stored on a storage medium, such as a hard drive, CD-ROM, flash drive or diskette, for reconstruction or playback at a later time.

The photographic image acquisition system 110 may also include an infrared imaging system or thermography system. Breast thermography through digital infrared imaging provides a temperature analysis of the surface of the breast. In general, areas having abnormally high metabolic activity and vascular circulation may be indicative of a region of interest.

From the photographic image and the three-dimensional parameters, if available, a surface map may be generated by the photographic image acquisition system 110. In some embodiments, the photographic image acquisition system 110 analyzes the photographic image and/or the surface map to identify regions of interest, which may be indicative of anomalous breast architecture or tissue, such as a tumor. For example, certain features that may be identified from the photographic image and/or the surface map of the breast include an ipsilateral skin texture, a contralateral skin texture, a skin color, a tissue dimpling, a nipple change, an inverted nipple, a lump, and a contralateral breast volume difference. Each of these features may be indicative of an anomalous tissue or breast architectures below the surface of the breast, along with other features that will be recognized by those having skill in the art. The thermography data may also be analyzed to determine further regions of interest. In general, areas having abnormally high metabolic activity and vascular circulation are indicative of cancerous or pre-cancerous tissue. The regions of interest may be determined through image analysis, segmentation, classification, learning algorithms, and other technologies. In some embodiments, the regions of interest may be identified manually by a medical professional viewing the photographic image. In such embodiments, the medical professional may indicate region of interest identifiers through a user interface.

A visual representation of the surface of the breast is generated by the photographic image acquisition system 110 and sent to the display system 160. The visual representation may be based on the photographic image, the surface map, and/or the three-dimensional data. For instance, the visual representation may be a representation of 3D surface map of the breast or a 2D contour map of the breast. The visual representation may also include markers or indicators for the regions of interest determined by the photographic image acquisition system 110 or processor or analyzer within the system 100 or the common device 180. Through a user interface, additional digital landmarks, crop marks, and fiducials may also be highlighted or indicated for display in the visual representation. The visual representation may also be modified to remove or mask any personally identifiable image data, such as the patient's face, from the photographs.

During acquisition of internal image data, such as by the ultrasound acquisition image system 140, the photographic image acquisition system 110 may continue to obtain updated photographic images of the breast. In an embodiment, the updated photographic images are continuously collected through a video recording camera. In such an embodiment, still images taken from the video feed may be used as the photographic image. In other embodiments, the updated photographic images are collected intermittently. When the updated photographic images are obtained, an updated visual representation of the surface of the breast is generated. For instance, if the ultrasound probe causes a depression or deformation in the breast, the updated visual representation of the breast will reflect the depression. Accordingly, the technician using the ultrasound probe will have an accurate view of the breast in its current form to further ensure a more accurate and thorough ultrasound imaging of the breast. In addition, analysis of the ultrasound images may reveal additional regions of interest to be incorporated into the visual representation.

Ultrasound image acquisition system 140 obtains an ultrasound image of a tissue of a patient, typically using an ultrasound probe, which is used to image a portion of a tissue of a patient within the field of view of the ultrasound probe. Ultrasound imaging system 140 obtains and displays an ultrasound image of a patient's anatomy within the field of view of the ultrasound probe and typically displays the image in real-time as the patient is being imaged. In some embodiments, the ultrasound image can additionally be stored on a storage medium, such as a hard drive, CD-ROM, flash drive or diskette, for reconstruction or playback at a later time.

In an embodiment, the system 100 may include an optional x-ray image acquisition system 170 that may be a tomosynthesis acquisition system that captures a set of projection images of a patient's breast as an x-ray tube scans a path around a portion of the breast. In other examples, the x-ray acquisition system 170 may be a mammography system or an x-ray computed tomography (CT) system. The set of projection images is subsequently reconstructed to a three-dimensional volume which may be viewed as slices or slabs along any plane. The three-dimensional volume may be stored locally on the x-ray image acquisition system 170 or in some embodiments in a Picture Archiving Communications System (PACS). Typically, the image format of the x-ray image is a DICOM format, however, skilled persons will understand that other image formats can be used. In other examples, other internal imaging modalities may be used in place of or in combination with the x-ray image acquisition system, such as a positron emission tomography (PET) system, a nuclear imaging system, a magnetic resonance imaging (MRI) system, or other similar imaging systems.

Tracking system 150 is in communication with navigation system 130 and tracks the physical position of the ultrasound imaging system 140 during imaging of the tissue of the patient. In some embodiments, tracking system 150 can be connected directly to navigation system 130 via a direct communication link or wireless communication link. Tracking system 150 tracks the position of transmitters connected to ultrasound imaging system 140 and provides navigation system 130 with data representing their coordinates in a tracker coordinate space. In some embodiments, tracking system 150 may be an optical tracking system comprising an optical camera and optical transmitters, however skilled persons will understand that any device or system capable of tracking the position of an object in space can be used. For example, skilled persons will understand that in some embodiments a radio-frequency (RF) tracking system can be used, comprising an RF receiver and RF transmitters.

Ultrasound imaging system 140 is configured for use with navigation system 130 by a calibration process using the tracking system 150. Transmitters that are connected to the ultrasound probe of ultrasound imaging system 140 can transmit their position to tracking system 130 in the tracker coordinate space, which in turn provides this information to navigation system 130. For example, transmitters may be positioned on the probe of ultrasound imaging system 140 so that tracking system 150 can monitor the position and orientation of the ultrasound probe and provide this information to navigation system 130 in the tracker coordinate space. Navigation system 130 can use this tracked position to determine the position and orientation of the ultrasound probe relative to the tracked position of the transmitters.

In some embodiments, configuration of the ultrasound image acquisition system 140 is performed using a configuration tool, where its position and orientation can be additionally tracked by tracking system 150. During configuration the configuration tool contacts the transducer face of the ultrasound probe of ultrasound imaging system 140 and tracking system 150 transmits information representing the position and orientation of the configuration tool in the tracker coordinate space to navigation system 130. Navigation system 130 can determine a configuration matrix that can be used to determine the position and orientation of the field of view of the ultrasound probe in the tracker coordinate space, based on the tracked position of the transmitters connected to the ultrasound probe. In alternative embodiments, a database having configuration data of a plurality of brands or models of various ultrasound probes can be used to pre-load a field of view configuration into navigation system 130 during configuration.

Once the ultrasound imaging system 140 is configured, the tissue of a patient can be imaged with the ultrasound imaging system 140. During ultrasound imaging, the tracking system 150 monitors the position and orientation of the ultrasound probe of ultrasound imaging system 140 and provides this information in the tracker co-ordinate space to navigation system 130. Since ultrasound imaging system 140 has been configured for use with navigation system 130, the navigation system 130 is able to determine a position and orientation of the field of view of the ultrasound probe of ultrasound imaging system 140.

Navigation system 130 can be configured to co-register an ultrasound image, along with the position and orientation information of the ultrasound probe, with the visual representation of the breast generated from the photographic image of the breast. In some embodiments, navigation system 130 can be configured to transform the position and orientation of the field of view of the ultrasound probe from the tracker coordinate space to a position and orientation in the visual representation, which may be the physical coordinates associated with three-dimensional space based on the acquired photographic image. In some examples, the photographic image is taken from a fixed position, providing for a coordinate system to be generating based on the position of the fixed camera. For example, when the visual representation is displayed, the location and orientation of the ultrasound probe may be displayed on the visual representation. In some embodiments, the visual representation is updated to reflect the portions of the breast that have been scanned or imaged by the ultrasound probe. Further, the displayed visual representation may be oriented to match the orientation and location of the ultrasound probe.

The x-ray image acquisition system 170 transmits the three-dimensional x-ray image volume to navigation system 130 via communication network 120, where x-ray images can be stored and viewed. Skilled persons will understand that the x-ray image of a patient can, in some embodiments, be stored locally on the x-ray image acquisition system 170 and accessed remotely by the navigation system 130 via communications network 120, and in other embodiments can be stored on a server in communication with navigation system 130 via communications network 120. In some embodiments, the x-ray image acquisition system 170 is housed in the same devices as the navigation system 130. Navigation system 130 displays the x-ray images obtained by x-ray imaging system and, once reconstructed for display on navigation system 130, the x-ray images can be reformatted and repositioned to view any image at any plane and any slice position or orientation. In some embodiments navigation system 130 displays multiple frames or windows on the same screen showing alternative positions or orientations of the x-ray-image slice.

Skilled persons will understand that the x-ray image volume obtained by x-ray imaging system 170 can be transmitted to navigation system 130 at any point in time and is not necessarily transmitted immediately after obtaining the x-ray image volume, but instead can be transmitted on the request of navigation system 130. In alternative embodiments, the x-ray image volume is transmitted to navigation system 130 by a transportable media device, such as a flash drive, CD-ROM, diskette, or other such transportable media device.

In some embodiments, navigation system 130 also accesses the ultrasound image, and in such embodiments ultrasound imaging system 140 is further connected to communication network 120 such that the ultrasound image can be transmitted to navigation system 130. In other embodiments, navigation system 130 can receive, or remotely access and copy, the ultrasound image, and in alternative embodiments, a copy of the ultrasound image can be stored on a server in communication with navigation system 130 and accessed remotely by navigation system 130.

Navigation system 130 may also be configured to co-register an ultrasound image with an x-ray image. In some embodiments, navigation system 130 can be configured to transform the position and orientation of the field of view of the ultrasound probe from the tracker coordinate space to a position and orientation in the x-ray image, for example, to DICOM coordinates. This can be accomplished by tracking the position and orientation of the ultrasound probe and transmitting this positional information in the tracker coordinate space to navigation system 130 and relating this positional information to the x-ray coordinate system. For example, in some embodiments, a user can select an anatomical plane within the x-ray image, and the user can then manipulate the position and orientation of a tracked ultrasound probe to align the field of view of the ultrasound probe with the selected anatomical plane. Once alignment is achieved, the associated tracker coordinate space coordinates of the ultrasound image can be captured. Registration of the anatomic axes (superior-inferior (SI), left-right (LR) and anterior-posterior (AP)) between the x-ray image and the tracker coordinate space can be determined from the relative rotational differences between the tracked ultrasound field of view orientation and the selected anatomical plane using techniques known to those of skill in the art.

The configuration of the navigation system 130 may further include the incorporation of landmarks or regions of interest within the x-ray image or the visual representation based on the photographic image. For example, the regions of interest determined by the photographic image acquisition system 110 may be incorporated or regions of interest may be selected using an interface permitting a user to select an anatomical target. In some embodiments, the landmark can be an internal tissue landmark, such as veins or arteries, and in other embodiments, the landmark can be an external landmark, such as a fiducial skin marker or external landmark, such as a nipple. The landmarks or regions of interest may then be incorporated into the visual representation so that the technician can locate them with the ultrasound probe. The relative differences between the coordinates of the target in the x-ray image, the coordinates associated with the visual representation, and the coordinates of the target in the tracker coordinate space are used to determine the translational parameters used to align the coordinate spaces. The plane orientation information acquired previously along with the coordinates based on the fixed camera can be combined with the translation parameters to provide a transformation matrix capable of co-registering the coordinate spaces.

Navigation system 130 may then use a transformation matrix to reformat the visual representation of the breast surface and/or an x-ray image being displayed so that surface of the breast and/or the slice of tissue being displayed is in the same plane and in the same orientation as the field of view of the ultrasound probe of ultrasound imaging system 140. Matched ultrasound and visual representations of the breast surface may then be displayed side-by-side. The matched ultrasound and x-ray images may also be displayed side-by-side, or directly overlaid in a single image viewing frame. In some embodiments, navigation system 130 can display additional x-ray images or visual representations of the surface of the breast in separate frames or positions on the display system 160. For example, the visual representation of the surface of the breast can be displayed from the same perspective as the field of view of the ultrasound probe. In some embodiments, annotations can be additionally displayed, representing, for example, the position of instruments imaged by ultrasound imaging system 140, such as biopsy needles, guidance wires, imaging probes, or other similar devices.

In other embodiments, the ultrasound image being displayed by the display system 160 can be superimposed on the slice of the x-ray image being displayed by the display system so that a user can view both the x-ray and ultrasound images simultaneously, overlaid on the same display. In some embodiments, navigation system 130 may enhance certain aspects of the superimposed ultrasound or x-ray images to increase the quality of the resulting combined image.

An exemplary method and system which may be used to navigate between a three dimensional image data set and an ultrasound feed, and to align coordinate systems to enable display of common reference points is described in further detail below, as well as in U.S. Pat. No. 9,019,262, the disclosure of which is incorporated by reference herein in its entirety.

Figure 2A:
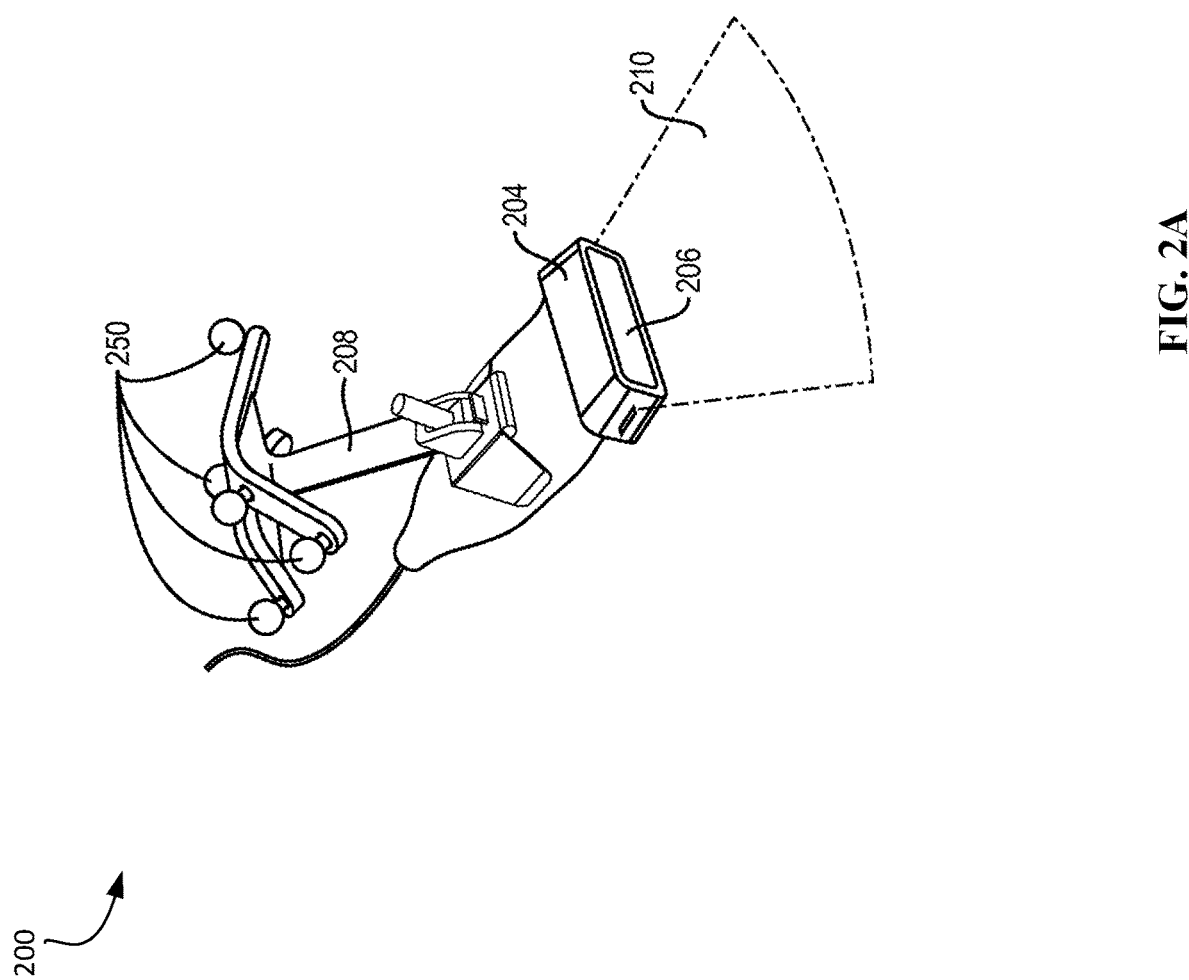
FIGS. 2A-2B depict a portion embodiment of an ultrasound system.
Figure 2B:
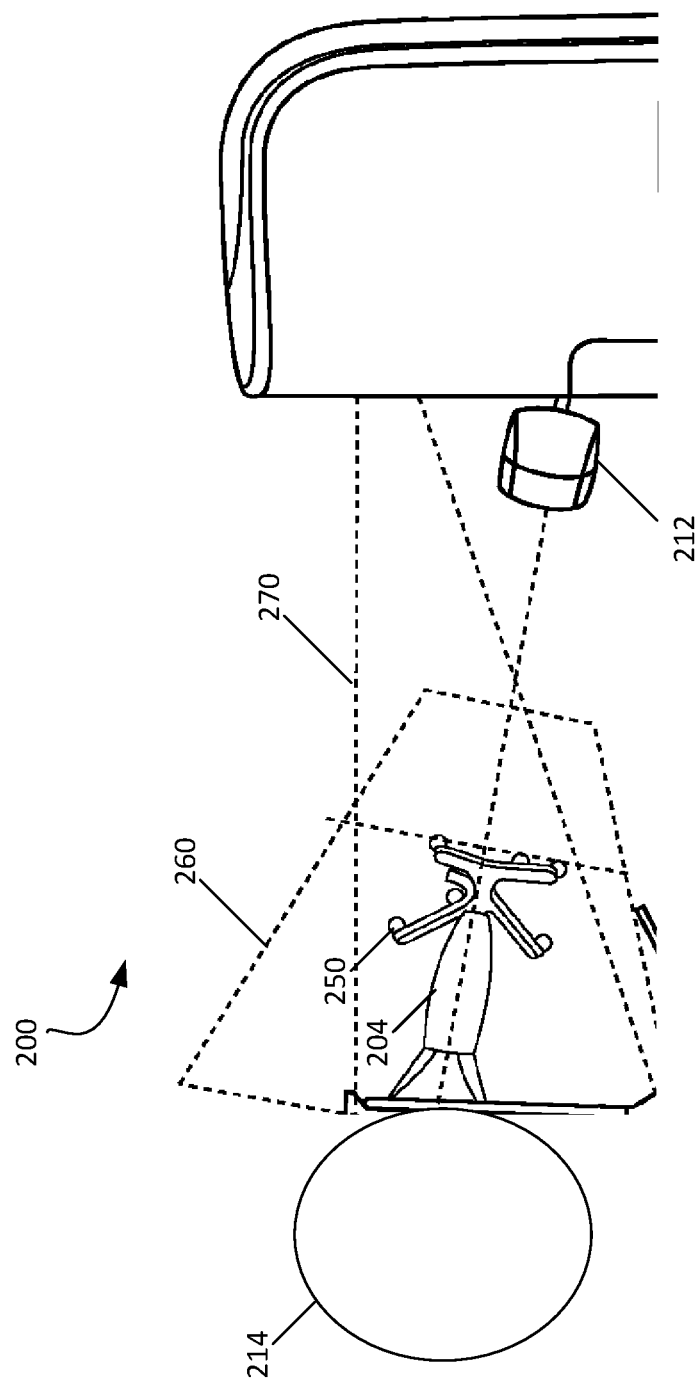

FIGS. 2A-2B depict a portion embodiment of an ultrasound system 200. The ultrasound system 200 includes an ultrasound probe 204 with a plurality of attached optical transmitters 250, as shown in FIG. 2A. The optical transmitters 250 are detected by an optical camera 212 mounted to a fixed surface. In some embodiments, a digital camera (not shown) for the photographic image acquisition system may be placed at substantially the same location as the optical camera 212. Optical camera 212 is connected to the communication network for transmitting the three-dimensional coordinate data of the plurality of optical transmitters to the navigation system 130 in the tracker coordinate space. Optical camera 212 monitors the position and orientation of ultrasound probe 204 by tracking ultrasound transmitters 250 and transmits this data to the navigation system via the communication network. In operation, as the technician directs the ultrasound probe 204 towards the target 214, such as a breast, the sound wave beam 210 is emitted from the transducer 206 into the target. During the examination, the location and orientation of the ultrasound probe 204 is tracked so as to record the location and angle of the sound wave beam, thus allowing correlation of an ultrasound image to that location and orientation.

In the embodiment shown, ultrasound probe 204 is engaged (e.g., via a support structure 208) to the ultrasound transmitters 250 that are tracked by optical camera 212 in the tracker coordinate space. The ultrasound transmitters 250 are optical transmitters tracked by optical camera 212, but other transmitter-receiver systems can be used. For example, in other embodiments, RF transmitters and receivers can be used to track the position and orientation of ultrasound probe 204 in the tracker coordinate space. Additionally, other orientations and positions of ultrasound transmitters 250 may be used to provide position and orientation information detectable by optical camera 212 and transmitted to navigation system 130. The ultrasound transmitters 250 may be removably connected to ultrasound probe 204 so as to provide the ability to configure any ultrasound probe with any shape of transducer 206, such as linear transducers, curvilinear transducers and array and phased array transducers. Different types of transducers may produce different types of sound wave beams 210.

In an additional embodiment, the co-registration of the ultrasound image feed with the surface images and/or tomosynthesis slices facilitates capture of ultrasound images at different planes and depths within the breast. Captured ultrasound images, each acquired from different depths within the breast, can be reconstructed to generate a three dimensional volume of ultrasound data. The present technology can be used to navigate the ultrasound probe to an appropriate location within a three dimensional volume acquired using tomosynthesis based on the surface image data. Once the probe is in the appropriate surface location, a sequence of ultrasound images may be obtained at varying depths by varying the strength of the ultrasound signal, thereby generating the information for the corresponding ultrasound image volume. It should be recognized that the present technology is not limited to generation of such a three dimensional ultrasound image volume at any particular location during an examination.

FIG. 2B further illustrates the different coordinate planes of the ultrasound transducer 260 (in a particular position), and the coordinate planes of the 3D tomosynthesis imaging geometry 270. The tracking system uses information provided by the transmitters on the probe to determine the orientation and position of the ultrasound probe in real-time, and therefore provides information related to the particular viewing plane associated with ultrasound feed at any instant.

The real time information provided via the ultrasound image feed can be used in a variety of ways. Manual manipulation of the ultrasound probe may be performed, with ultrasound image feed also being provided on the ultrasound display (or a portion of the workstation display allocated to the ultrasound image). As the ultrasound probe approaches the region of interest, a visual or audible cue may be provided to the user, allowing the user to view the mass more carefully and/or capture a representative image for later review. Other types of feedback may also be provided based on the ultrasound scanning. For example, audible or visual feedback may be provided based on the velocity of the ultrasound probe. A particular tone may be sounded at a predetermined speed of the ultrasound probe, and that tone may change in pitch as the velocity of the ultrasound probe changes. Audible or visual feedback may also be provided regarding the orientation or position of the ultrasound probe to aid in the ultrasound image acquisition. The feedback may also indicate a type of probe or characteristics of the ultrasound beam to be used for a region of interest. For example, the feedback may indicate that an 18 MHz ultrasound probe should be utilized for a particular region of interest.

Figure 3A:
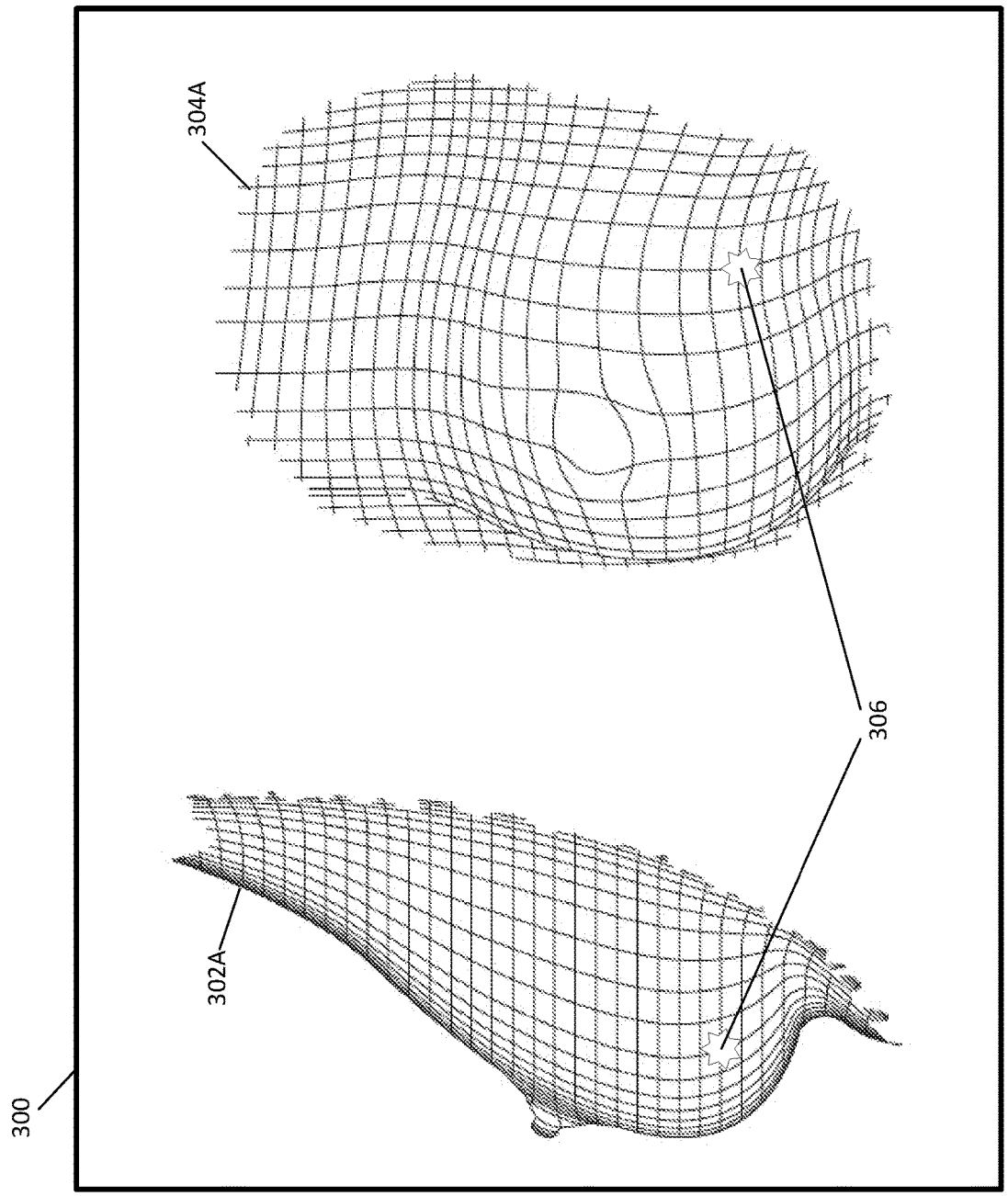
FIGS. 3A-3C depict examples of a displayed visual representation of a breast during acquisition of internal image data.
Figure 3B:
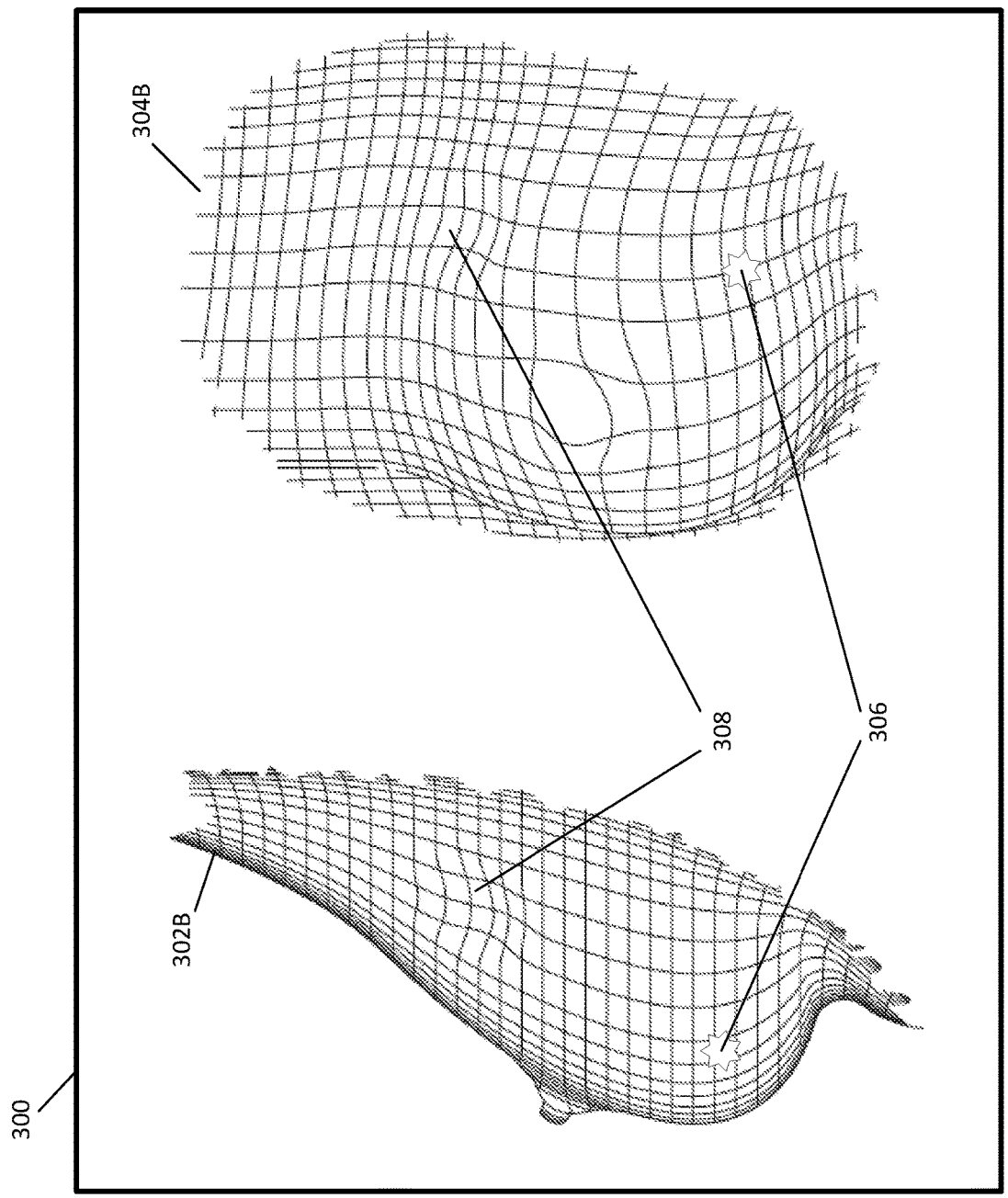
Figure 3C:
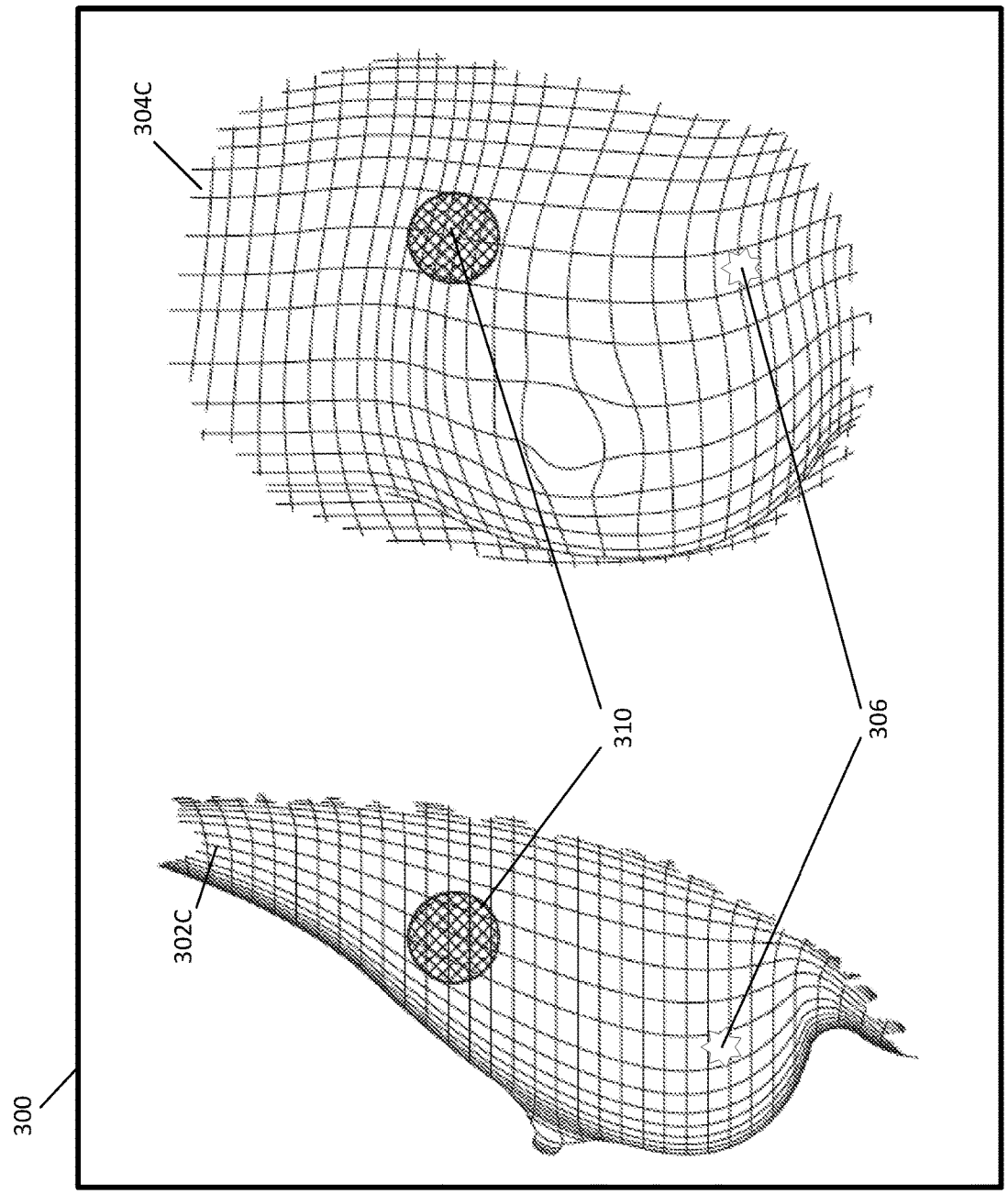

FIGS. 3A-3C depict examples of a displayed visual representation of a breast during acquisition of internal image data, such as with an ultrasound probe. FIG. 3A depicts a display 300 (e.g., the display system 160 of FIGS. 1A-1B) showing two visual representations of the surface of the breast. The first visual representation 302A shows a side view of the surface of the breast, and the second visual representation 304A shows a front view of the surface of the breast. Each visual representation is based on a surface map of the breast. On each visual representation, a surface indicator 306 is displayed. The surface indicator 306 indicates a region of interest that was determined based on the photographic image, the three-dimensional data, the thermographic data, and/or by manual identification through a user interface. The display 300 is placed proximate to the medical professional performing the ultrasound imaging so that the medical professional can see the visual representations and understand where the regions of interest are located. While not shown in the figures, the visual representation may be overlaid with the photographic image of the breast to allow the technician to see natural landmarks on the breast, such as moles or other skin conditions, e.g., to use as reference points. In some embodiments, the visual representations of the breast will also display axilla tissue or other portions of the body surrounding the breast.

FIG. 3B depicts updated visual representations 302B, 304B during acquisition of the internal image data with an ultrasound probe. During the internal image acquisition, the ultrasound probe may alter the shape of the breast, such as by causing a depression 308. The updated visual representations 302B, 304B reflect the current shape of the breast, including showing the depression 308 or other changes in shape of the breast during the examination. Accordingly, the medical professional can see the updates and adjust the ultrasound probe as needed.

FIG. 3C depicts updated visual representations 302C, 304C during acquisition of the internal image data with an ultrasound probe. In the updated visual representations 302C, 304C, a scanned area 310 that has been scanned by the ultrasound probe is symbolized in the visual representations 302C, 304C. As shown, the scanned area 310 is indicated by a cross-hatched area in the updated visual representations 302C, 304C. The scanned area 310 may also be indicated by a color change, shading, or any other visual indicator to show which areas of the breast have been scanned by the ultrasound probe. Accordingly, during acquisition of the internal image data, the medical professional is able to view which portions of the breast have not yet been scanned. For example, where the entire breast is to be scanned, the entire breast would be covered by the cross-hatching of scanned area 310 upon completion of the ultrasound scan.

While two visual representations 302, 304 are depicted as being displayed in FIGS. 3A-3C, in some embodiments only one visual representation is displayed. In such embodiments, the visual representation may virtually rotate such that the visual representation is from the same perspective as the ultrasound beam being emitted from the ultrasound probe. The virtual movement of the visual representation may also be recorded and correlated with the acquired ultrasound images for later playback and analysis so that a medical professional will be able to better understand the angle and location of the ultrasound probe for each acquired ultrasound image. Further, a real-time view of the collected ultrasound images may also be displayed in display 300 or in a separate display.

Figure 4A:
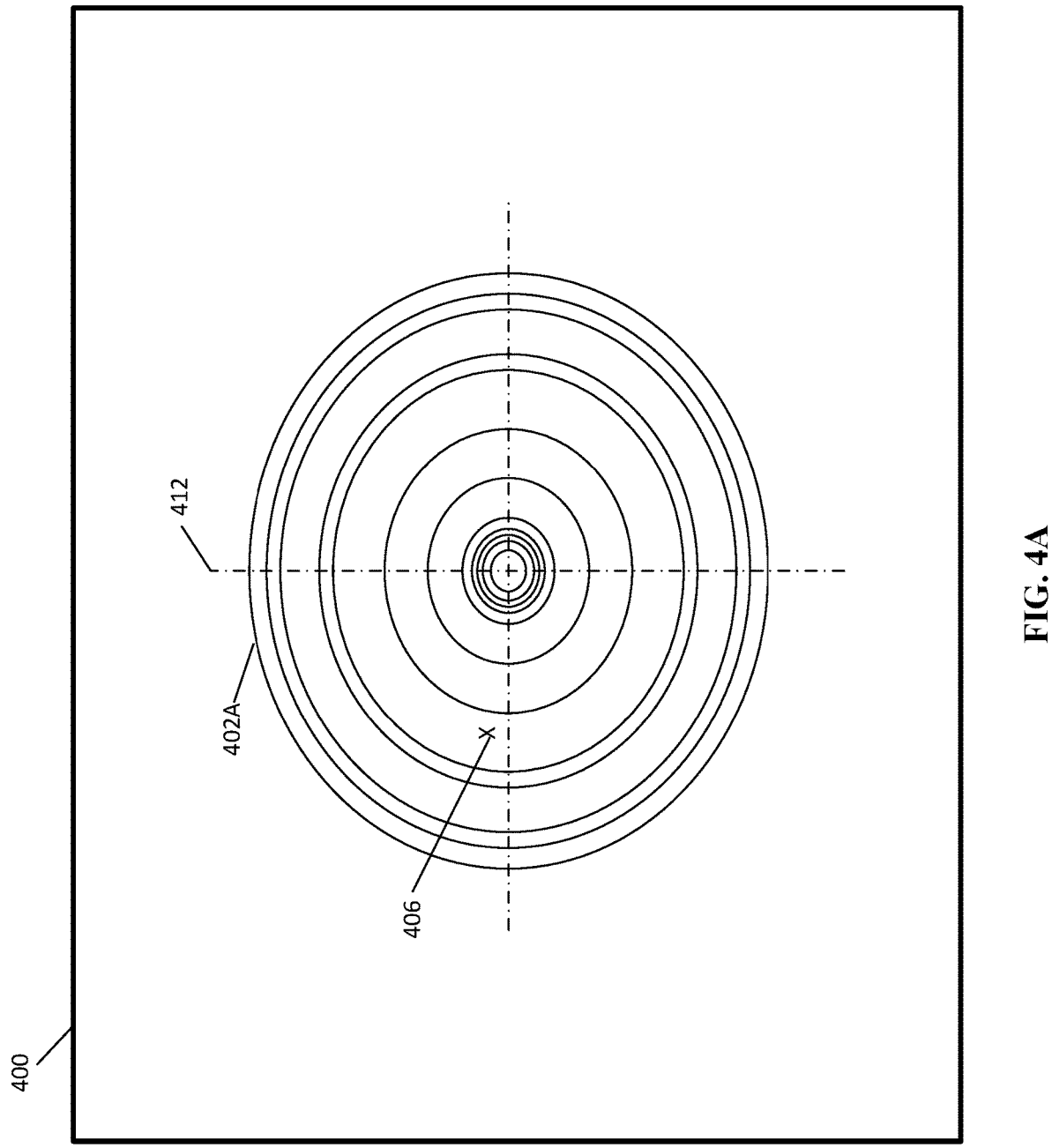
Figure 4C:
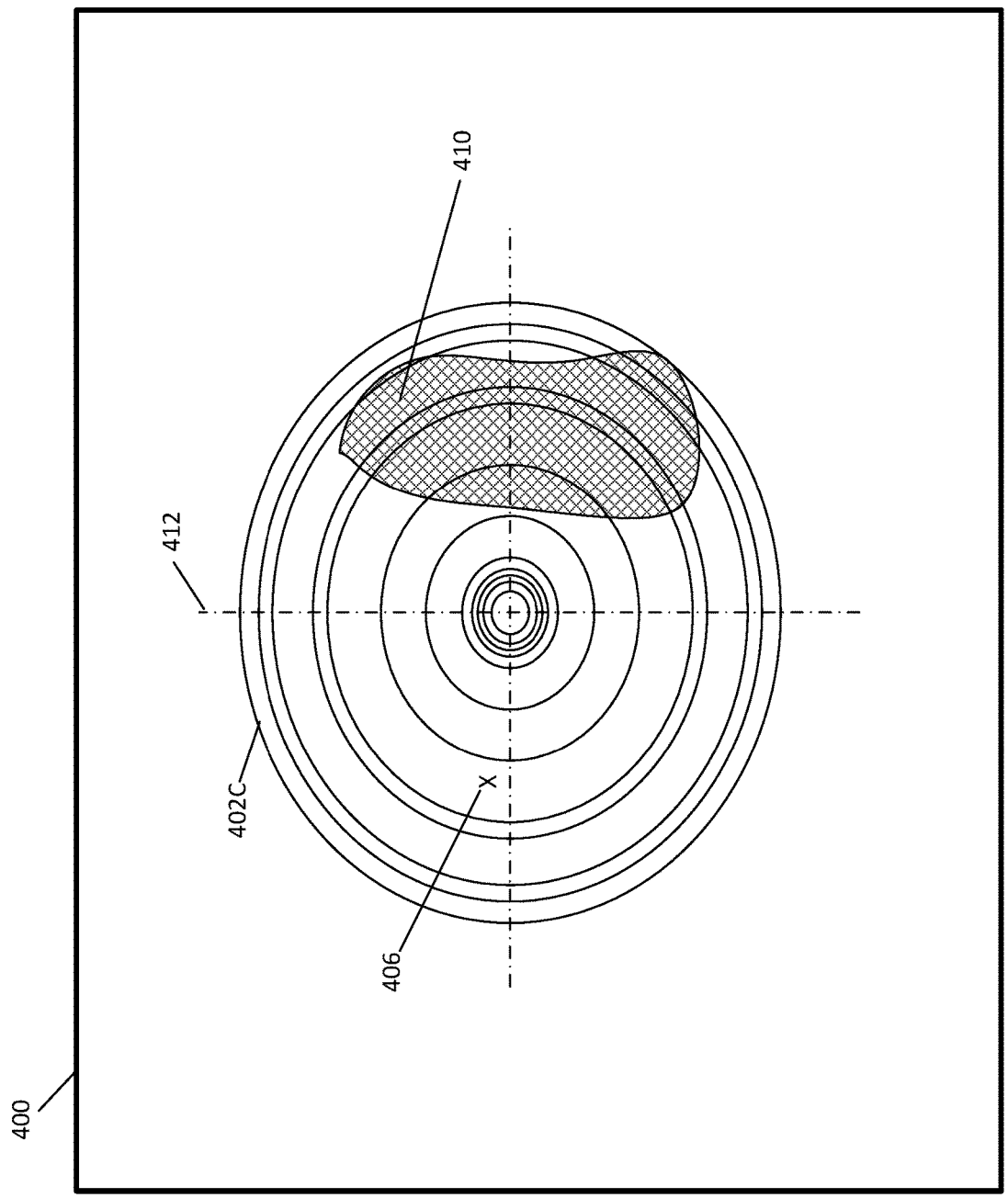

FIGS. 4A-4C depict examples of a displayed visual representation of a breast during acquisition of internal image data, such as with an ultrasound probe. FIG. 4A depicts a display 400 showing a visual representation 402A of the breast. The visual representation 402A is a contour map of the breast from a front view of the breast. The simplified contour map visual representation 402A may be used rather than the surface maps shown in FIGS. 3A-3C where computing resources are limited or less information is required for the ultrasound scan. The visual representation 402A includes a surface indicator 406 indicating a point or region of interest. The visual representation 402A may also include quadrant lines 412 that provide a further reference marker for the medical professional conducting the ultrasound exam. In some embodiments, the contour map visual representation 402A of the breast will also display axilla tissue or other portions of the body surrounding the breast.

FIG. 4B depicts updated visual representation 404B during acquisition of the internal image data with an ultrasound probe. During the internal image acquisition, the ultrasound probe may alter the shape of the breast, such as by causing a depression 408. The updated visual representation 402B reflects the current shape of the breast, including showing the depression 408 or other changes in shape of the breast during the examination. Accordingly, the medical professional can see the updates and adjust the ultrasound probe as needed.

FIG. 4C depicts another updated visual representation 404C during acquisition of the internal image data with an ultrasound probe. In the updated visual representation 404C, a scanned area 410 that has been scanned by the ultrasound probe is depicted as a cross-hatched area. The scanned area 410 may also be indicated by a color change, shading, or any other visual indicator to show which areas of the breast have been scanned by the ultrasound probe. Accordingly, during acquisition of the internal image data, the medical professional is able to view which portions of the breast have not yet been scanned. For example, where the entire breast is to be scanned, the entire breast would be covered by the cross-hatching of scanned area 410 upon completion of the ultrasound scan.

Figure 5A:
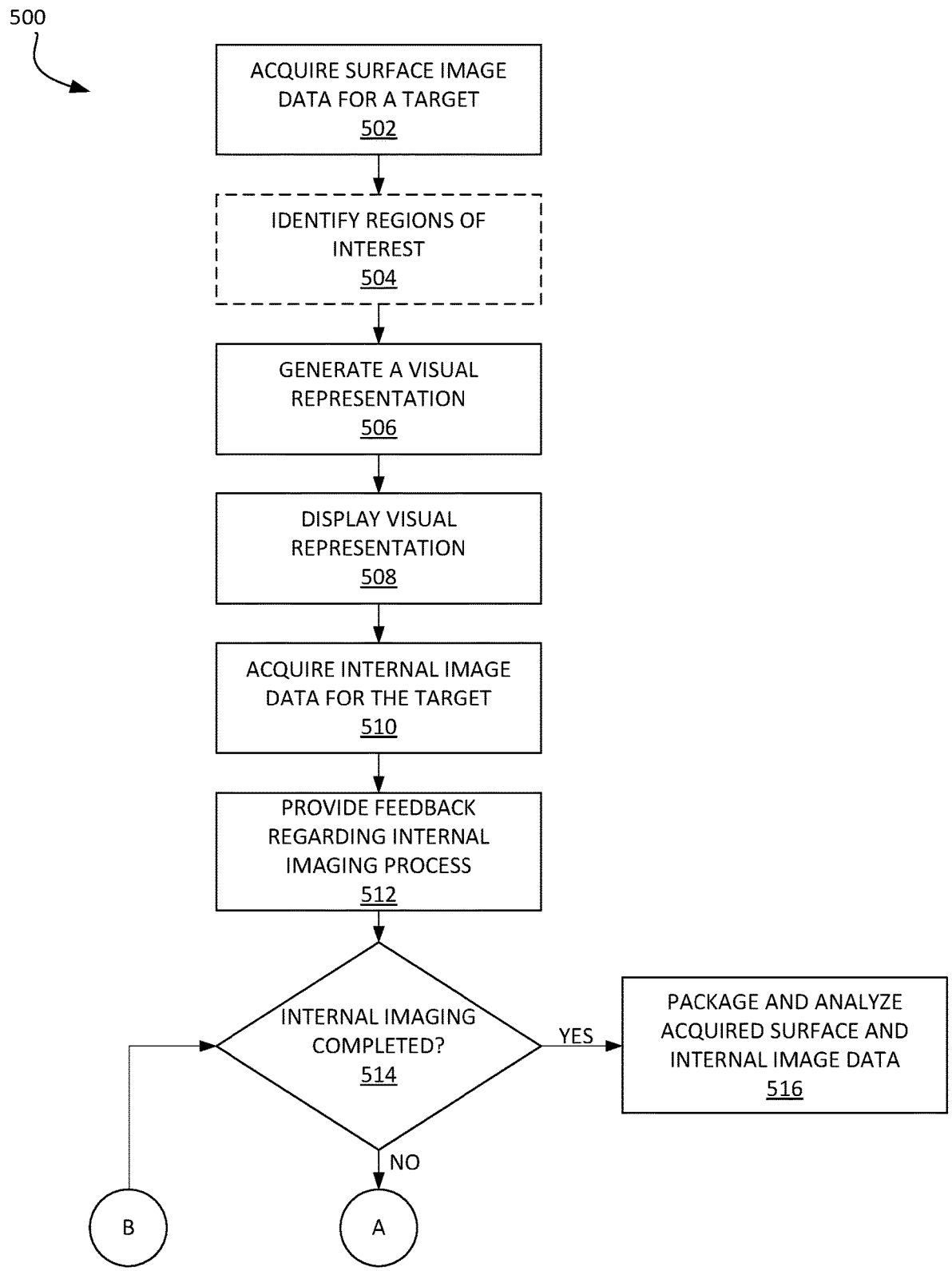
FIGS. 5A-5B depict an example of a method for imaging a target.
Figure 5B:
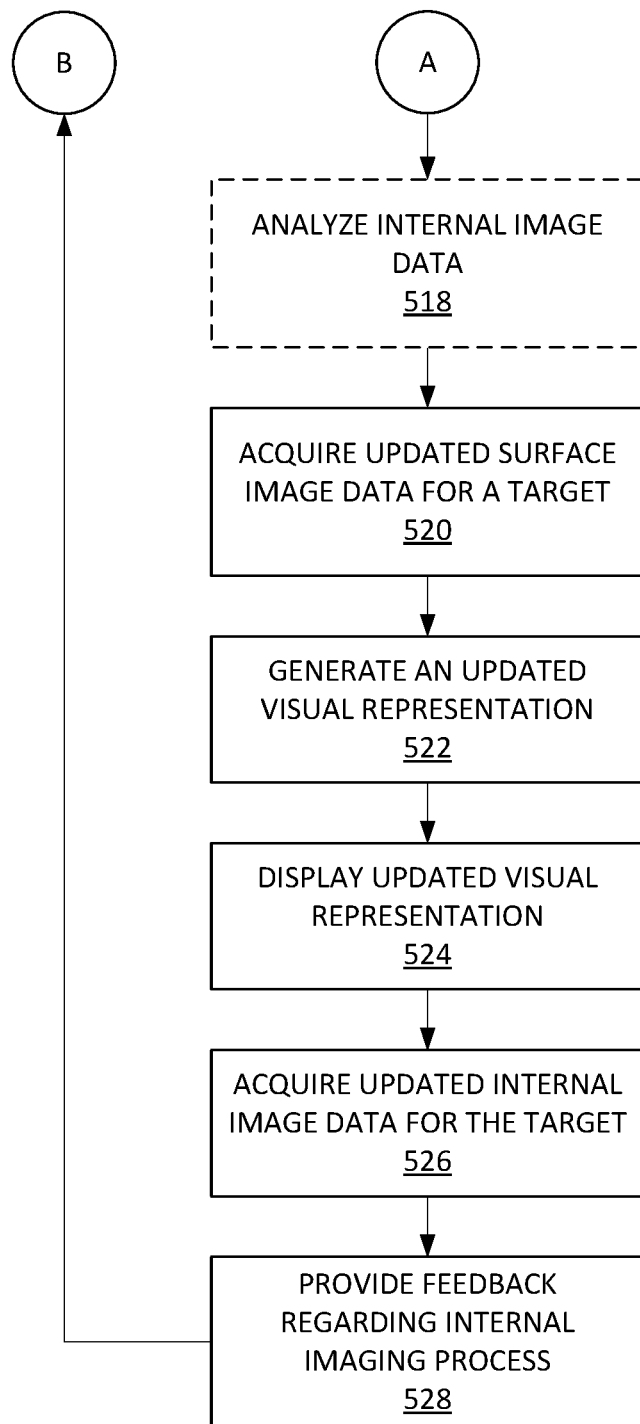

FIGS. 5A-5B depict an example of a method 500 for imaging a target, such as a breast. At operation 502, a surface image of a breast is acquired using a first imaging modality. As discussed above, the first imaging modality may include digital photography, stereoscopic photography, structured light stereoscopic photography, and/or infrared imaging, or any combination thereof. From an analysis of the acquired surface image, one or more regions of interest may optionally be identified at operation 504. For example, certain features that may be identified from the photographic image and/or the surface map of the breast may be indicative of an anomalous tissue or breast architectures below the surface of the breast, as discussed above. The regions of interest may be determined through image analysis, segmentation, classification, learning algorithms, and other technologies. In some embodiments, the regions of interest may be identified manually by a medical professional viewing the surface image data through a user interface in a workstation.

At operation 506, a visual representation of the surface of the breast is generated based on the surface image data. Generation of the visual representation may also include generating a surface map from the surface image data. The generated visual representation may also include markers or indicators for the regions of interest determined in operation 504. A medical professional may also utilize further digital landmarks, crop marks, and fiducials to add to the visual representation through a user interface in a workstation. Once the visual representation is generated, it is displayed on a display screen at operation 508 as guidance for a medical professional conducting an internal imaging examination, such as an ultrasound examination.

At operation 510, internal image data for the target is acquired. The internal image data for the target may be acquired through the use of a manually controlled ultrasound probe. During the acquisition of the internal image data, the location, angle, and other characteristics of the ultrasound probe are tracked so that the acquired internal image data can be co-registered or correlated with the coordinates of the visual representation of the surface of the breast. At operation 512, feedback can be provided regarding the internal imaging process. For example, from the tracked characteristics of the ultrasound probe, audible or visual feedback can be provided, as discussed above.

At operation 514, a determination is made as to whether the internal imaging examination has been completed. For example, if the examination required a scan of the full breast with the ultrasound probe, a determination can be made as to whether the full breast has actually been scanned by analyzing the ultrasound image data correlated with the visual representation of the surface of the breast. In other examples, the determination may be made by determining whether the medical professional has manually ended the examination, such as by pressing an END button in a user interface.

If the internal imaging has not been completed, the method 500 proceeds to operation 518, where the internal image data may be optionally analyzed to determine any additional regions of interests that should be further examined by the ultrasound probe. At operation 520, updated surface image data is acquired. The updated surface image data may be acquired in the same manner as in operation 502. The updated surface image data may also be continuously collected. For instance, the cameras utilized to capture the surface image data may record video to provide a continuous image feed. An updated visual representation is then generated at operation 520 based on the updated surface image data and the additional regions of interest identified in operation 518, if any. The updated visual representation indicates a current view of the target, thus reflecting any real-time depressions, deformations, or other shape changes in the target. The updated visual representation may also include indicators for the original regions of interest and also indicators for the additional regions of interest. Further, the updated visual representation may also include coloring, shading, or other markers to indicate the portions of the target that have already been scanned by the ultrasound probe. The updated visual representation is then displayed on the display screen at operation 524. In some embodiments, the updated visual representation may also be displayed in a manner to match the perspective of the ultrasound probe.

At operation 526, updated internal image data for the target is acquired. The internal image data may be acquired in the same manner as in operation 510. Feedback on the internal imaging process may again be provided at operation 528, similar to operation 512. The process then returns to operation 514 where another determination is made as to whether the internal imaging examination has been completed. If the examination has not completed, the method proceeds to perform another loop. In an embodiment, the method continuously acquires updated surface image data and generates and displays the updated visual representations during the examination. The feedback may also be continuously provided for the duration of the examination.

If at operation 514, the examination is complete, the method flows to operation 516 where the surface image data and the internal image data is packaged and analyzed. In some embodiments, the totality of the surface image data and the internal image data acquired during the examination is used to generate a three-dimensional model of the breast. By tracking the location of the ultrasound probe during the examination and correlating that location with the coordinates of the surface image data, the 3D model is able to provide a robust and spatially accurate volumetric ultrasound image. The 3D model can then be viewed by a physician or other specialist to determine a potential risk for cancer or other ailments. In some examples, a learning algorithm or other automated analysis is applied to the 3D model to determine a potential cancer risk score or further identify architectures in the target for medical review. Due to the processing requirements in analyzing the model, such analysis may be performed by a server or other cloud services. In a simplified application, a positive or a negative output may be generated based on the analysis of the surface image data and the internal image data. Patients receiving the positive output would be cleared from further examination, whereas patients receiving a negative output would be recommended for additional testing. Such a simplified model is particularly useful in areas where complex or radiologic cancer screenings are limited. By bringing the present technology to such areas, efficient cancer screenings using digital photography and ultrasound probes can be achieved for populations where such screenings are generally not readily available.

In some examples, the internal image data is analyzed during the examination and marked if there is internal image data indicative of anomalous structures. Then, only the marked internal images are saved and incorporated into the 3D model, thus saving processing and memory requirements.

Figure 6:
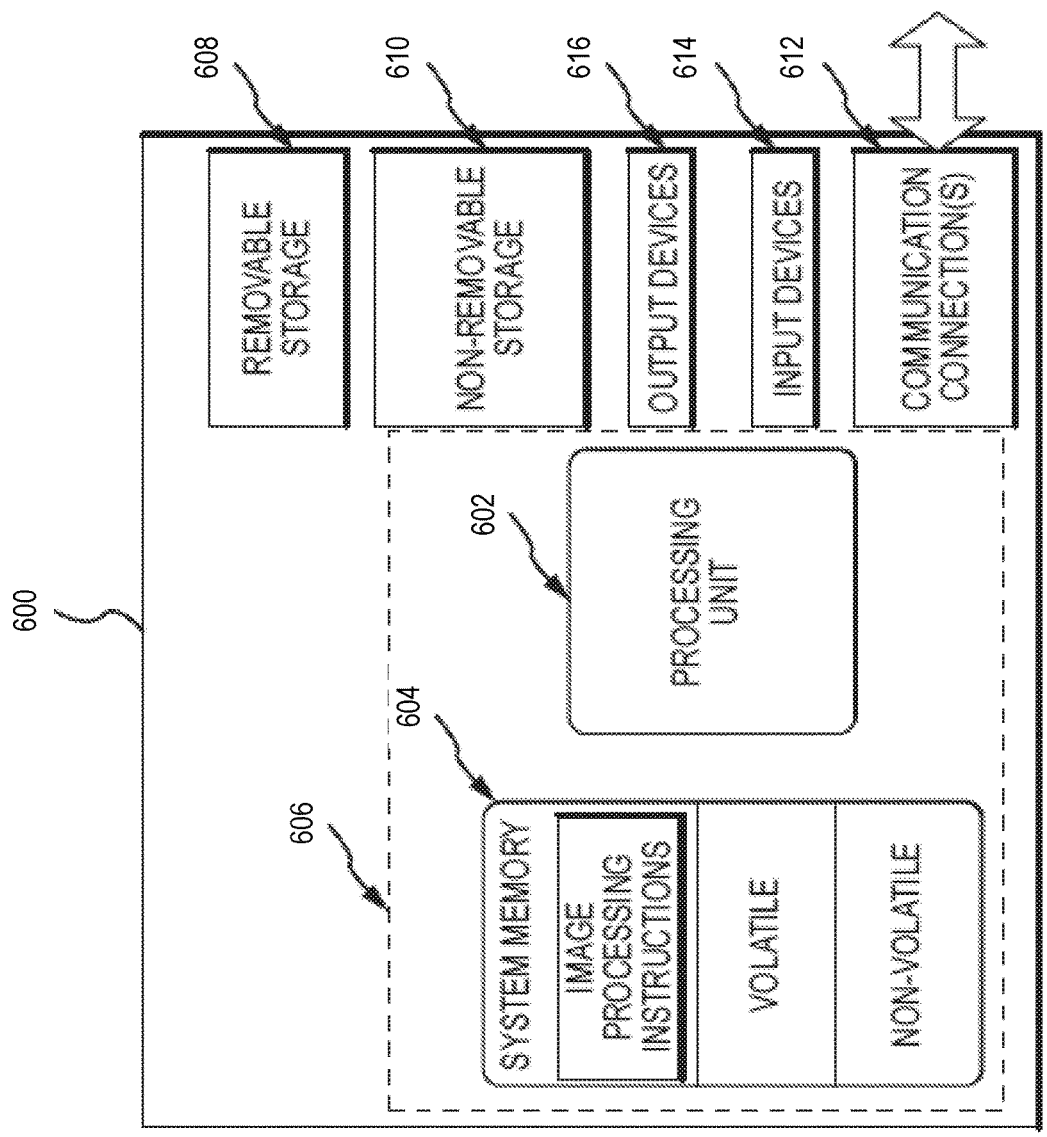
FIG. 6 illustrates one example of a suitable operating environment in which one or more of the present examples can be implemented.

FIG. 6 illustrates one example of a suitable operating environment 600 in which one or more of the present embodiments can be implemented. This operating environment may be incorporated directly into the imaging systems disclosed herein, or may be incorporated into a computer system discrete from, but used to control, a the imaging systems described herein. This is only one example of a suitable operating environment and is not intended to suggest any limitation as to the scope of use or functionality. Other well-known computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 600 typically includes at least one processing unit 602 and memory 604. Depending on the exact configuration and type of computing device, memory 604 (storing, among other things, instructions to perform the image acquisition and processing methods disclosed herein) can be volatile (such as RAM), non-volatile (such as ROM, flash memory, etc.), or some combination of the two. This most basic configuration is illustrated in FIG. 6 by dashed line 606. Further, environment 600 can also include storage devices (removable, 608, and/or non-removable, 610) including, but not limited to, magnetic or optical disks or tape. Similarly, environment 600 can also have input device(s) 614 such as touch screens, keyboard, mouse, pen, voice input, etc., and/or output device(s) 616 such as a display, speakers, printer, etc. Also included in the environment can be one or more communication connections 612, such as LAN, WAN, point to point, Bluetooth, RF, etc.

Operating environment 600 typically includes at least some form of computer readable media. Computer readable media can be any available media that can be accessed by processing unit 602 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 600 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein comprise such modules or instructions executable by computer system 600 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 600 is part of a network that stores data in remote storage media for use by the computer system 600.

Figure 7:
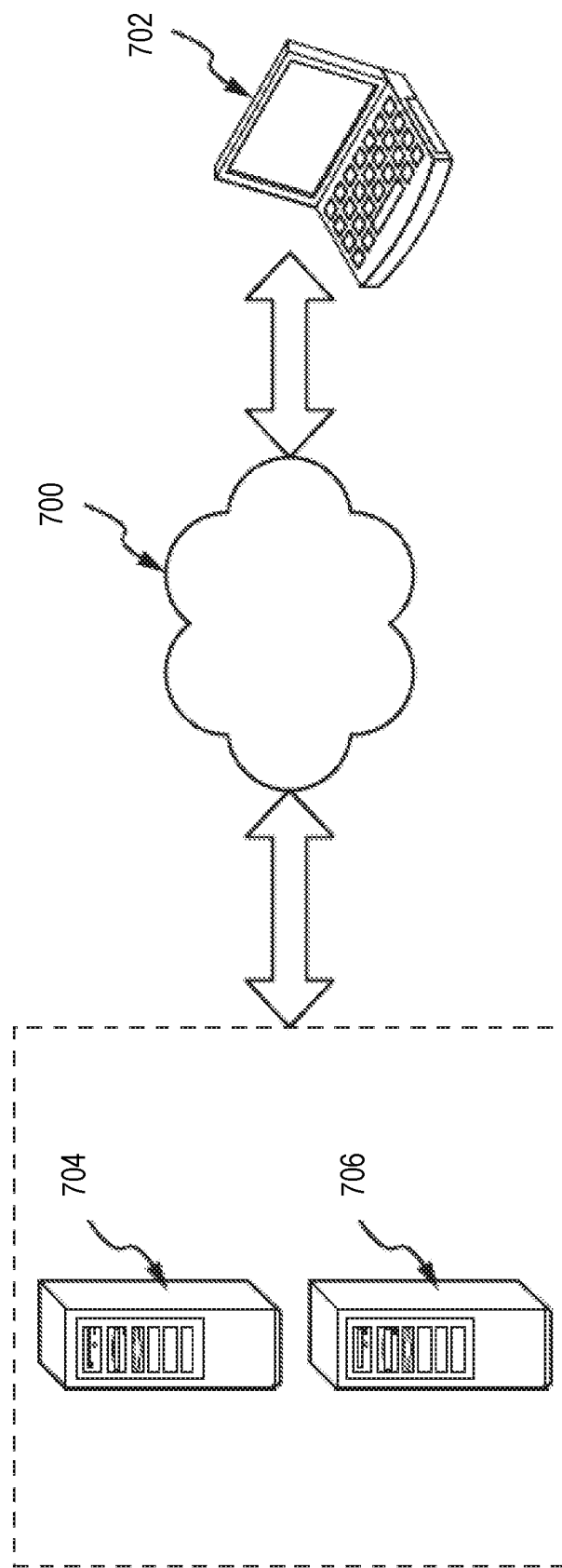
FIG. 7 is an embodiment of a network in which the various systems and methods disclosed herein may operate.

FIG. 7 is an embodiment of a network 700 in which the various systems and methods disclosed herein may operate. In embodiments, a client device, such as client device 702, may communicate with one or more servers, such as servers 704 and 706, via a network 708. In embodiments, a client device may be a standalone device may be a portable of fixed work station (e.g., work station 180 depicted in FIG. 1B). The client device may also include or incorporate a laptop, a personal computer, a smart phone, a PDA, a netbook, or any other type of computing device, such as the computing device in FIG. 6. In embodiments, servers 704 and 706 may also be any type of computing device, such as the computing device illustrated in FIG. 6. Network 708 may be any type of network capable of facilitating communications between the client device and one or more servers 704 and 706. For example, the surface image data and the internal image data may be acquired locally via the imaging systems and communicated to another computing device(s) for further processing, such as an image acquisition workstation or a cloud-based service. Examples of such networks include, but are not limited to, LANs, WANs, cellular networks, and/or the Internet.

In embodiments, the various systems and methods disclosed herein may be performed by one or more server devices. For example, in one embodiment, a single server, such as server 704 may be employed to perform the systems and methods disclosed herein, such as the methods for imaging discussed herein. Client device 702 may interact with server 704 via network 708. In further embodiments, the client device 702 may also perform functionality disclosed herein, such as scanning and image processing, which can then be provided to servers 704 and/or 706.

In alternate embodiments, the methods and systems disclosed herein may be performed using a distributed computing network, or a cloud network. In such embodiments, the methods and systems disclosed herein may be performed by two or more servers, such as servers 704 and 706. Although a particular network embodiment is disclosed herein, one of skill in the art will appreciate that the systems and methods disclosed herein may be performed using other types of networks and/or network configurations.

The embodiments described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some embodiments of the present technology with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. Embodiments according to the technology may also combine elements or components of those that are disclosed in general but not expressly exemplified in combination, unless otherwise stated herein. The scope of the technology is defined by the following claims and any equivalents therein.

What is claimed is:

1. A method for imaging a breast of a patient, the method comprising:
   acquiring a photographic image of a surface of the breast;
   based on the photographic image, generating a 3D surface map of the breast;
   displaying a visual representation of the breast, wherein the visual representation is a 3D surface map of the breast;
   identifying a region of interest on the surface of the breast based on at least one of the visual representation or the photographic image;
   displaying the visual representation of the breast with an indicator indicating the identified region of interest;
   acquiring ultrasound images of the breast with an ultrasound probe; and
   during acquisition of the ultrasound images:
      updating the display of the visual representation based at least in part on the acquired ultrasound images;
      acquiring an updated photographic image of the breast while the breast is deformed by the ultrasound probe during the acquisition of the ultrasound images; and
      displaying an updated visual representation the breast, wherein updated visual representation shows the deformation of the breast.

2. The method of claim 1, wherein updating the display of the visual representation includes displaying in the visual representation portions of the breast scanned by the ultrasound probe.

3. The method of claim 1, further comprising analyzing the acquired ultrasound images of the breast to identify an additional region of interest of the breast for scanning with the ultrasound probe, and wherein updating the display of the visual representation includes displaying, in the visual representation, another indicator for the additional region of interest of the breast.

4. The method of claim 1, further comprising generating feedback regarding the ultrasound probe approaching the region of interest.

5. The method of claim 1, wherein the photographic image is a stereoscopic structured light image of the breast.

6. The method of claim 1, further comprising analyzing at least one of the acquired ultrasound images and the photographic image to determine an anomalous breast architecture.

7. The method of claim 6, further comprising generating a three-dimensional model based on the ultrasound images, wherein the three-dimensional model includes an indicator indicating the location of the anomalous breast architecture.

8. The method of claim 1, further comprising analyzing at least one of the acquired ultrasound images and the photographic image to generate a cancer risk score for the breast.

9. The method of claim 1, wherein the region of interest is an anatomical landmark, and the anatomical landmark is at least one of an ipsilateral skin texture, a contralateral skin texture, a skin color, a tissue dimpling, an inverted nipple, a mole, or a lump.

10. The method of claim 1, wherein the visual representation further includes the photographic image.

11. The method of claim 1, further comprising virtually rotating the visual representation such that the visual representation is from the same perspective as a field of view of the ultrasound probe.

12. A system for imaging a breast of a patient, the system comprising:
    a camera;
    an ultrasound probe;
    a display;
    at least one processor; and
    memory operatively coupled to the at least one processor, the memory storing instructions that, when executed by the at least one processor, perform a set of operations including:
        generating a surface map of the breast based on a photographic image acquired by the camera;
        identifying a region of interest on the surface of the breast;
        generating a visual representation of the surface map and a surface indicator on the visual representation, wherein the surface indicator indicates the identified region of interest;
        displaying, on the display, the visual representation with the surface indicator;
        acquiring ultrasound images of the breast from the ultrasound probe;
        during acquisition of the ultrasound images:
            acquiring an updated photographic image of the breast while the breast is deformed by the ultrasound probe during the acquisition of the ultrasound images; and
            displaying an updated visual representation the breast, wherein updated visual representation shows the deformation of the breast.

13. The system of claim 12, wherein the operations further comprising generating an update to the display of the visual representation based on the acquired ultrasound images, wherein the update includes a graphical representation on the visual representation representing a portion of the breast scanned by the ultrasound probe.

14. The system of claim 12, wherein the operations further comprising generating an update to the display of the visual representation based on the acquired ultrasound images, wherein the update includes a graphical representation on the visual representation representing another region of interest of the breast to be scanned with the ultrasound probe.

15. The system of claim 12, wherein the set of operations further comprises analyzing at least one of the acquired ultrasound images and the photographic image to determine an anomalous breast architecture.

16. The system of claim 12, wherein identifying the region of interest is based on at least one of an ipsilateral a skin texture, a contralateral skin texture, a skin color, a tissue dimpling, a nipple change, an inverted nipple, a lump, and a contralateral breast volume difference.

17. The system of claim 12, wherein the set of operations further comprises, based on one or more of the surface map and the acquired ultrasound images, generating feedback regarding at least one of an angle of the ultrasound probe, an orientation of the ultrasound probe, a position of the ultrasound probe, and a scan velocity of the ultrasound probe.

18. The system of claim 12, further comprising a speaker and wherein the set of operations further comprises:
    analyzing the acquired ultrasound images to identify an internal region of interest; and
    based on the analysis of the acquired ultrasound images, sending an audio signal to the speaker to provide an audible feedback based on the probe approaching an internal region of interest.

19. A method for imaging a breast of a patient, the method comprising:
    acquiring a photographic image of a breast using a camera;
    displaying a visual representation of the breast, wherein the visual representation is based at least on the photographic image;
    scanning the breast with an ultrasound probe;
    while scanning, tracking the location of the ultrasound probe and updating the displayed visual representation based on the tracked location of the ultrasound probe;
    analyzing ultrasound images acquired during scanning of the breast to identify an internal region of interest; and
    displaying, on the visual representation during acquisition of the ultrasound images, an indicator for the internal region of interest.

20. The method of claim 19, further comprising virtually rotating the visual representation based on at least one of an angle of the ultrasound probe, an orientation of the ultrasound probe, or a position of the ultrasound probe.

* * * * *